United States Patent
Nishide et al.

(10) Patent No.: US 11,555,028 B2
(45) Date of Patent: Jan. 17, 2023

(54) ORGANIC COMPOUND AND PHOTOELECTRIC CONVERSION ELEMENT

(71) Applicant: CANON KABUSHIKI KAISHA, Tokyo (JP)

(72) Inventors: Yosuke Nishide, Kawasaki (JP); Naoki Yamada, Inagi (JP); Hiroki Ohrui, Kawasaki (JP); Hironobu Iwawaki, Yokohama (JP); Hirokazu Miyashita, Ebina (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 94 days.

(21) Appl. No.: 16/163,757

(22) Filed: Oct. 18, 2018

(65) Prior Publication Data

US 2019/0119258 A1  Apr. 25, 2019

(30) Foreign Application Priority Data

Oct. 25, 2017 (JP) .............................. JP2017-206030

(51) Int. Cl.
    *C07D 403/10* (2006.01)
    *C07D 409/14* (2006.01)
    (Continued)

(52) U.S. Cl.
    CPC .......... *C07D 403/10* (2013.01); *C07D 209/08* (2013.01); *C07D 401/14* (2013.01);
    (Continued)

(58) Field of Classification Search
    CPC ................ C07D 403/10; C07D 401/14; C07D 209/08; C07D 409/14; C07D 405/14;
    (Continued)

(56) References Cited

U.S. PATENT DOCUMENTS 7,597,955 B2  10/2009 Takiguchi et al.
8,378,339 B2  2/2013 Nomura et al.
(Continued)

FOREIGN PATENT DOCUMENTS

JP  2005082701 A  *  3/2005  ............. H01L 51/50
JP  2006120763 A  *  5/2006  ............. C09K 11/06
(Continued)

OTHER PUBLICATIONS

JP2005082701A, Machine Translation, Yanai, Mar. 2005 (Year: 2005).*
JP2006120763A, Machine Translation, Kato, May 2006 (Year: 2006).*
Yamada et al., U.S. Appl. No. 16/051,724, filed Aug. 1, 2018.
(Continued)

*Primary Examiner* — Devina Pillay
(74) *Attorney, Agent, or Firm* — Venable LLP

(57) ABSTRACT

An organic compound represented by the following general formula [1] is excellent in thermal stability.

[1]

(Continued)

In the general formula [1], $R_1$ to $R_{12}$ are each independently selected from the group consisting of a hydrogen atom and a substituent. Symbol A is selected from the group consisting of a divalent residue of naphthalene, phenanthrene, fluorene, benzofluorene, dibenzofluorene or spirofluorene, and a heteroarylene group having 4 to 12 carbon atoms. Symbol B is selected from the group consisting of an arylene group having 6 to 25 carbon atoms and a heteroarylene group having 4 to 12 carbon atoms. Symbol n is an integer of 0 to 3.

20 Claims, 3 Drawing Sheets

(51) Int. Cl.

| | | |
|---|---|---|
| *C07D 405/14* | (2006.01) | |
| *H01L 51/44* | (2006.01) | |
| *H01L 51/00* | (2006.01) | |
| *C07D 401/14* | (2006.01) | |
| *C07D 209/08* | (2006.01) | |
| *H04N 5/378* | (2011.01) | |
| *H01L 27/30* | (2006.01) | |
| *H01L 51/42* | (2006.01) | |
| *H04N 5/374* | (2011.01) | |

(52) U.S. Cl.
CPC ......... *C07D 405/14* (2013.01); *C07D 409/14* (2013.01); *H01L 51/0072* (2013.01); *H01L 51/441* (2013.01); *H01L 27/307* (2013.01); *H01L 51/0073* (2013.01); *H01L 51/0074* (2013.01); *H01L 51/4253* (2013.01); *H01L 51/4273* (2013.01); *H04N 5/374* (2013.01); *H04N 5/378* (2013.01)

(58) Field of Classification Search
CPC ............... H01L 51/441; H01L 51/0072; H01L 51/4253; H01L 51/0052; H01L 51/0073; H01L 51/0074; H01L 51/4273; H01L 27/307; H04N 5/374; H04N 5/378
See application file for complete search history.

(56) References Cited

U.S. PATENT DOCUMENTS

| | | |
|---|---|---|
| 8,637,860 B2 | 1/2014 | Nomura et al. |
| 8,847,141 B2 | 9/2014 | Fukuzaki et al. |
| 8,847,208 B2 | 9/2014 | Mitsui et al. |
| 2007/0057250 A1 | 3/2007 | Takiguchi et al. |
| 2008/0035965 A1 | 2/2008 | Hayashi et al. |
| 2009/0058279 A1* | 3/2009 | Takeda ................... C09K 11/06 313/504 |
| 2012/0298846 A1 | 11/2012 | Nomura et al. |
| 2013/0184458 A1* | 7/2013 | Sawada ............... H01L 51/0067 544/209 |
| 2014/0291634 A1* | 10/2014 | Shin ...................... C09K 11/06 257/40 |
| 2018/0108691 A1* | 4/2018 | Kamatani ........... H01L 51/0081 |
| 2018/0342559 A1 | 11/2018 | Kamatani et al. |

FOREIGN PATENT DOCUMENTS

| | | | |
|---|---|---|---|
| JP | 2011-225544 A | 11/2011 | |
| JP | 2013-538440 A | 10/2013 | |
| JP | 2017-143133 A | 8/2017 | |
| KR | 2017-0037135 A | 4/2017 | |
| WO | 2012/004765 A1 | 1/2012 | |
| WO | WO-2016194337 A1 * | 12/2016 | .......... H01L 51/005 |
| WO | 2017/149958 A1 | 9/2017 | |
| WO | 2018/016354 A1 | 1/2018 | |

OTHER PUBLICATIONS

Miyashita et al., U.S. Appl. No. 16/114,686, filed Aug. 28, 2018.
Nishide et al., U.S. Appl. No. 16/106,534, filed Aug. 21, 2018.
Yamada et al., U.S. Appl. No. 16/130,029, filed Sep. 13, 2018.
Yamada et al., U.S. Appl. No. 16/243,500, filed Jan. 9, 2019.
Notice of Reasons for Refusal in Japanese Application No. 2017-206030 (dated Aug. 2021).
JP 2017-143133, U.S. Patent Application Publication No. 2018/0342559 A1.
JP 2011-225544, U.S. Pat. No. 8,378,339 B2 U.S. Pat. No. 8,637,860 B2 U.S. Pat. No. 8,847,141 B2 U.S. Pat. No. 8,847,208 B2.
JP 2013-538440, WO 2012/004765 A2.

* cited by examiner

ORGANIC COMPOUND AND PHOTOELECTRIC CONVERSION ELEMENT

BACKGROUND

Field of the Disclosure

The present invention includes, as various embodiments thereof, an organic compound, as well as an electronic element and a photoelectric conversion element using the organic compound, and also includes an imaging device and an imaging apparatus using the photoelectric conversion element.

Description of the Related Art

In recent years, technologies of organic electronic devices are advancing and attempting to exhibit a wide variety of spreads, but among those devices, organic EL (electroluminescent) devices (or elements) have advanced researches for application thereof to displays, and have reached even commercialization. An organic EL element is an element which converts electric energy to light energy and emits light.

On the other hand, a photoelectric conversion element is an element which receives light from the outside and converts its energy to electric energy. A solid-state imaging device having a sensor including a plurality of photoelectric conversion elements, which are two-dimensionally arrayed therein, for utilizing their photoelectric conversion properties is widely used. In recent years, a photoelectric conversion element which contains an organic compound in a photoelectric conversion layer of the photoelectric conversion element has been progressively developed, but in order to make practical use, there is room for improvement in conversion efficiency, durability and the like.

In Patent Literature 1 (U.S. Patent Application Publication No. 2008/0035965, hereinafter referred to as "PTL 1"), it is reported that a charge blocking layer for preventing injection of electric charges from an electrode is used between the photoelectric conversion layer having photoelectric conversion capability and the electrode. In addition, in Patent Literature 2 (U.S. Patent Application Publication No. 2012/0298846, hereinafter referred to as "PTL 2"), an example is reported such that an element after sealed was subjected to heat treatment (annealing treatment) at high temperature to have shown a reduced dark current.

In Patent Literature 3 (U.S. Patent Application Publication No. 2007/0057250, hereinafter referred to as "PTL 3"), on the other hand, an organic compound a-1 having an indole structure, as well as an organic EL element using the organic element, is described. Further, in Patent Literature 4 (U.S. Patent Application Publication No. 2014/0291634, hereinafter referred to as "PTL 4"), a blue light-emitting compound b-1 having an indole structure, as well as an organic EL element using the organic compound, is described.

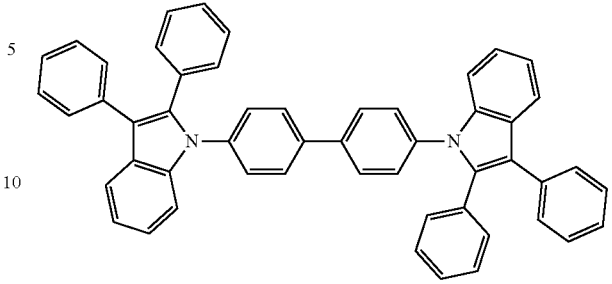

a-1

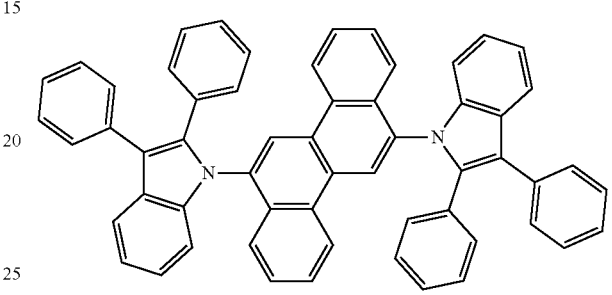

b-1

The organic compound a-1 described in PTL 3 is used as a host material for a light emitting layer of an organic EL element. It is a compound of which molecule is highly symmetric and shows a high crystallinity is high, hence being less stable. Accordingly, degradation of element characteristics due to crystallization is concerned, in annealing at high temperature, or in application of a large thermal load when the photosensor is mounted.

The organic compound b-1 described in PTL 4 is used as a blue light-emitting material for a light emitting layer of an organic EL element, and has absorption in a visible light region. Accordingly, decline of photoelectric conversion efficiency due to partial absorption of incident light is concerned, when the compound is used for an electron blocking layer of an organic photoelectric conversion element.

SUMMARY

The present invention provides, as an embodiment thereof, an organic compound which is excellent in thermal stability and has no absorption in a visible light region.

This embodiment provides an organic compound that is represented by the following general formula [1].

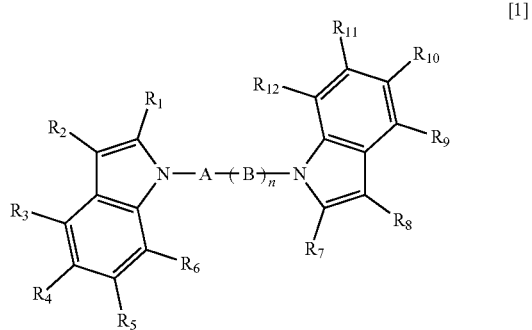

[1]

In the general formula [1], $R_1$ to $R_{12}$ are each independently selected from the group consisting of a hydrogen atom, a halogen atom, a cyano group, an alkyl group, an aryl group having 6 to 18 carbon atoms, and a heteroaryl group having 3 to 15 carbon atoms. The alkyl group may have a halogen atom as a substituent. The aryl group having 6 to 18 carbon atoms and/or the heteroaryl group having 3 to 15 carbon atoms may have a halogen atom, a cyano group, an alkyl group and/or an alkoxy group, as a substituent.

Symbol A is selected from the group consisting of a divalent residue of naphthalene, phenanthrene, fluorene, benzofluorene, dibenzofluorene or spirofluorene, and a heteroarylene group having 4 to 12 carbon atoms. The structure of A may have an alkyl group as a substituent.

Symbol B is selected from the group consisting of an arylene group having 6 to 25 carbon atoms and a heteroarylene group having 4 to 12 carbon atoms. The structure of B may have an alkyl group as a substituent.

Symbol n is an integer of 0 to 3. When n is 2 or larger, the respective B's may be the same as or different from each other.

Further features of the present invention will become apparent from the following description of exemplary embodiments with reference to the attached drawings.

DESCRIPTION OF THE EMBODIMENTS

Figure 1:
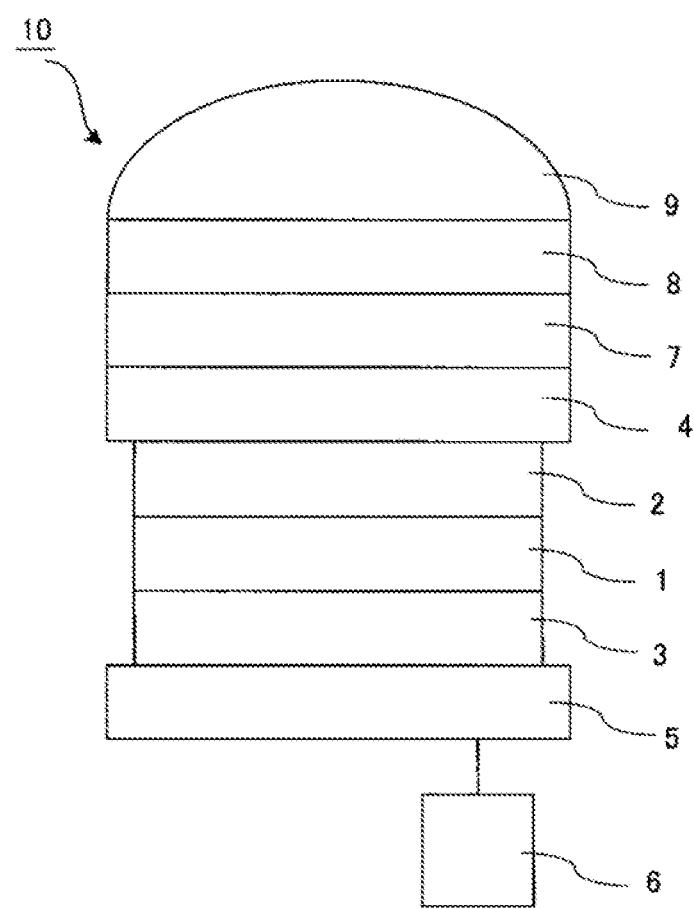
FIG. 1 is a schematic cross-sectional view illustrating one example of a photoelectric conversion element according to an embodiment of the present invention.

Preferred embodiments of the present invention will now be described in detail with reference to the accompanying drawings.

Organic Compound According to Embodiment of Present Invention

An organic compound according to one embodiment of the present invention (hereinafter referred to as "organic compound of present embodiment") is represented by the following general formula [1].

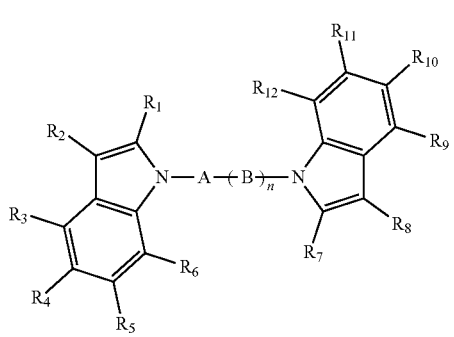

[1]

In the general formula [1], $R_1$ to $R_{12}$ are each independently selected from the group consisting of a hydrogen atom, a halogen atom, a cyano group, an alkyl group, an aryl group having 6 to 18 carbon atoms, and a heteroaryl group having 3 to 15 carbon atoms. The alkyl group may have a halogen atom as a substituent. The aryl group having 6 to 18 carbon atoms and the heteroaryl group having 3 to 15 carbon atoms may have a halogen atom, a cyano group, an alkyl group and/or an alkoxy group as a substituent.

The halogen atoms include a fluorine atom, a chlorine atom, a bromine atom and an iodine atom. The halogen atom is preferably a fluorine atom.

Examples of the alkyl group include a methyl group, an ethyl group, a n-propyl group, an iso-propyl group, a n-butyl group, a sec-butyl group and a tert-butyl group. The alkyl group is preferably a tert-butyl group, from the viewpoint of sublimability and thermal stability.

Examples of the aryl group having 6 to 18 carbon atoms include a phenyl group, a naphthyl group, a biphenyl group, a fluorenyl group, a terphenyl group, an anthracenyl group, a phenanthrenyl group, a pyrenyl group and a fluoranthenyl group; and are preferably the phenyl group, the naphthyl group, the biphenyl group, the fluorenyl group and the terphenyl group.

Examples of the heteroaryl group having 3 to 15 carbon atoms include pyridine, pyrimidine, pyrazine, triazine, quinoline, isoquinoline, quinoxaline, phenanthroline, thiophene, benzothiophene, dibenzothiophene, furan, benzofuran, dibenzofuran, thiazole, thiadiazole, oxazole and oxadiazole; and are preferably pyridine, pyrimidine, pyrazine, triazine, thiophene, benzothiophene, furan, benzofuran, thiazole, thiadiazole, oxazole and oxadiazole.

The halogen atom which the alkyl group may possess includes a fluorine atom, a chlorine atom, a bromine atom and an iodine atom. The halogen atom is preferably a fluorine atom.

Examples of the alkyl group which the aryl group having 6 to 18 carbon atoms and the heteroaryl group having 3 to 15 carbon atoms may possess include a methyl group, an ethyl group, a n-propyl group, an isopropyl group, a n-butyl group, a sec-butyl group and a tert-butyl group. Preferably, the alkyl group is a tert-butyl group, from the viewpoint of sublimability and thermal stability.

Examples of the alkoxy group which the aryl group having 6 to 18 carbon atoms and the heteroaryl group having 3 to 15 carbon atoms may possess include a methoxy group, an ethoxy group, an iso-propoxy group, a n-butoxy group, a sec-butoxy group and a tert-butoxy group; and the methoxy group is preferable.

It is preferable that at least one, preferably at least four of $R_1$ to $R_{12}$, or at least one of $R_1$, $R_2$, $R_7$ and $R_8$ is not a hydrogen atom. Here, the species that is not a hydrogen atom is the above described halogen atom, cyano group, alkyl group, aryl group having 6 to 18 carbon atoms, or heteroaryl group having 3 to 15 carbon atoms. In addition, it is preferable that the species that is not a hydrogen atom is a tert-butyl group or a group having a tert-butyl group.

Symbol A is selected from the group consisting of a divalent residue of naphthalene, phenanthrene, fluorene, benzofluorene, dibenzofluorene or spirofluorene, and a heteroarylene group having 4 to 12 carbon atoms. The structure of A may have an alkyl group as a substituent.

Examples of the benzofluorene include benzo[a]fluorene, benzo[b]fluorene and benzo[c]fluorene; and benzo[c]fluorene is preferable.

Examples of the dibenzofluorene include dibenzo[a,g]fluorene, dibenzo[a,h]fluorene, dibenzo[a,i]fluorene, dibenzo[b,g]fluorene, dibenzo[b,i]fluorene and dibenzo[c,g]fluorene; and dibenzo[c,g]fluorene is preferable.

Examples of the spirofluorene include 9,9'-spirobifluorene, spiro[benzo[c]fluorene-7,9'-fluorene], spiro[dibenzo[c,g]fluorene-7,9'-fluorene]; and 9,9'-spirobifluorene is preferable.

Examples of the heteroarylene group having 4 to 12 carbon atoms include divalent residues of pyridine, pyrimidine, pyrazine, pyridazine, quinoline, isoquinoline, quinoxaline, thiophene, benzothiophene, furan, benzofuran, dibenzothiophene and dibenzofuran; and the divalent residue of pyridine, pyrimidine, pyrazine, quinoline, isoquinoline, quinoxaline, dibenzothiophene or dibenzofuran is preferable.

Examples of the alkyl group which A may possess include a methyl group, an ethyl group, a n-propyl group, an iso-propyl group, a n-butyl group, a sec-butyl group and a tert-butyl group; and the methyl group and the tert-butyl group are preferable.

A preferably has a bulky and highly stable structure, from the viewpoint of the sublimability and thermal stability, and amorphous film stability; and specifically, a divalent residue of naphthalene, fluorene or spirofluorene is more preferable.

Symbol B is selected from the group consisting of an arylene group having 6 to 25 carbon atoms and a heteroarylene group having 4 to 12 carbon atoms. The structure of B may have an alkyl group as a substituent.

Specific examples of the arylene group having 6 to 25 carbon atoms include the divalent residues described as examples of the above described A, in addition to a divalent residue of benzene. Specific examples of the heteroarylene group having 4 to 12 carbon atoms and the alkyl group which B may possess are the same as those described as examples of the above described A. It is preferable that B has such a structure as to have a small molecular weight and high stability, and is preferably a fused ring, from the viewpoint of the sublimability and thermal stability; and a divalent residue of benzene or naphthalene is preferable.

Symbol n is an integer of 0 to 3, and is preferably 0 or 1. When n is 2 or larger, the respective B's may be the same as or different from each other.

As for the organic compound of the present embodiment, it is preferable that A is a divalent residue of naphthalene, phenanthrene, fluorene, benzofluorene, dibenzofluorene or spirofluorene, and B is an arylene group having 6 to 25 carbon atoms. In addition, as for the organic compound of the present embodiment, it is preferable that A is a divalent residue of naphthalene or phenanthrene, and B is the divalent residue of the naphthalene or the phenanthrene. In addition, as for the organic compound of the present embodiment, it is preferable that at least one of A and B is a divalent residue of fluorene, benzofluorene, dibenzofluorene or spirofluorene. In addition, as for the organic compound of the present embodiment, it is preferable that at least one of A and B is a heteroarylene group having 4 to 12 carbon atoms.

<<Properties of Organic Compound of Present Embodiment>>

The organic compound of the present embodiment has the following properties of (1) to (5).

(1) High stability of amorphous film
(2) High thermal stability
(3) Wide band-gap performance
(4) High electron-blocking property
(5) High hole-transporting performance Each of the properties will be described below.

(1) High Stability of Amorphous Film

In general, an aromatic compound has a high planarity of its molecular skeleton, and accordingly has a strong intermolecular interaction; and molecular packing tends to be easily promoted. Here, the molecular packing means that molecules overlap each other due to the intermolecular interaction. In addition, in a molecular structure having a high symmetric property, molecules tend to be easily aligned in a solid state, and accordingly the molecular packing tends to be more easily promoted in synergy with the intermolecular interaction. This molecular packing leads to crystallization of the film, and accordingly is not preferable.

The compound of the present embodiment is a compound which includes an indole ring moiety and spacer moieties represented by A and B. The indole skeleton has a structure having a high planarity but a low symmetric property (point group: C1), and accordingly can suppress the molecular packing. On the other hand, a carbazole skeleton which is generally and widely used has the high planarity and the high symmetric property (point group: C2v), and accordingly can be said to be a compound which tends to cause the molecular packing. In addition, there is a method of introducing a large number of substituents, as one of methods for suppressing the molecular packing, but it is preferable that the molecular weight of a basic skeleton is smaller, from the viewpoint of the aggravation of the sublimability, which is associated with an increase in the molecular weight. From this point as well, the indole skeleton in the organic compound of the present embodiment is preferable.

<Comparison between Exemplary Compound A1 of Organic Compound of the Present Embodiment and Comparative Compound a-1>

An Exemplary Compound A1 of the organic compound of the present embodiment is represented by the following structural formula.

A1

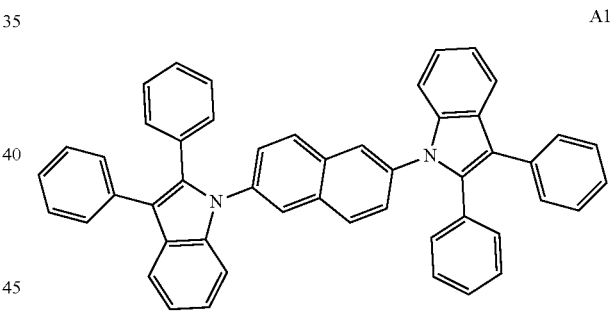

A comparative compound a-1 is represented by the following structural formula.

a-1

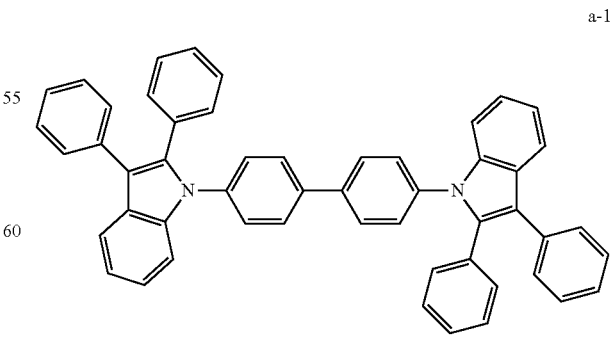

The spacers of A and B in the general formula [1] will be compared between the exemplary compound of the organic compound of the present embodiment (hereinafter referred to as "exemplary compound of the present embodiment") A1 and the comparative compound a-1, from the viewpoint of the rotation axis and the π conjugate plane. Structural formula [2] represents a simplified formula of the Exemplary Compound A1 of the present embodiment, and structural formula [3] represents a simplified formula of the comparative compound a-1.

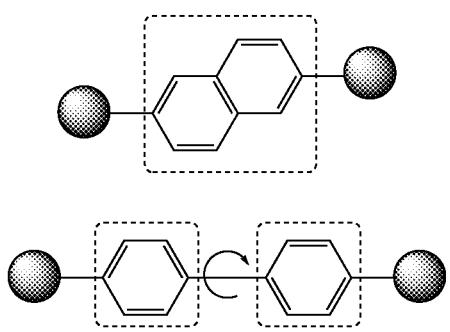

[2]

[3]

The structural formula [2] of the exemplary compound including a naphthalene spacer in the present embodiment has no rotation axis in the spacer, and has a fused ring structure. On the other hand, the structural formula [3] related to a comparative compound including a biphenyl spacer has one rotation axis in the spacer, and does not have a fused ring structure. In order to increase the glass transition temperature, it is known to suppress the fluidity in the film, by enlarging the π conjugate plane and the like. Specifically, the spacer having only the biphenyl group does not have a fused ring structure in the spacer, and accordingly the π conjugate plane is not sufficiently enlarged. As a result, the glass transition temperature of the compound is low. A high glass transition temperature means that the amorphous film can be stably maintained even at a higher temperature. The Exemplary Compound A1 of the present embodiment has the fused ring structure in the spacer, and accordingly can suppress the fluidity in the film better than comparative compound a-1, and the glass transition temperature is enhanced. Accordingly, the Exemplary Compound A1 of the present embodiment has a higher stability of the amorphous film than the comparative compound a-1. In addition, the glass transition temperature tends to be enhanced by reduction in the rotational site in the spacer.

In addition, the glass transition temperatures of the Exemplary Compound A1 of the present embodiment and the comparative compound a-1 were evaluated by differential scanning calorimetry (DSC) measurement. At the time of the DSC measurement, approximately 2 mg of a sample was enclosed in an aluminum pan and was rapidly cooled from a high temperature exceeding the melting point, and thereby the sample was converted into an amorphous state. Subsequently, the sample was heated at a rate of temperature rise of 20° C./min, and thereby the glass transition temperature was measured. In addition, DSC 204 F1 made by NETZSCH Japan K.K. was used as a measuring apparatus. As a result of the measurement, the glass transition temperature of the comparative compound a-1 was not detected. This result means that a stable amorphous film is unlikely to form. On the other hand, the glass transition temperature of the Exemplary Compound A1 of the present embodiment was detected, and was 148° C. Accordingly, the Exemplary Compound A1 of the present embodiment is a material that tends to easily form a stable amorphous thin film and has high thermal stability.

As a method for suppressing the molecular packing, there is a method of introducing a substituent which is preferably a bulky alkyl group, besides the above described method. The number of the bulky alkyl groups to be introduced is preferably 2 to 8, and more preferably is 2 to 6.

Furthermore, as for another method for suppressing the molecular packing, there is an introduction of a fluorene ring, a benzofluorene ring, a dibenzofluorene ring or a spirofluorene ring, in any of which the molecule is relatively bulky in the center and has a highly stable structure. The planarity can be suppressed in a structure in which a methyl group is introduced at a position represented by the 9th position of the fluorene ring; a structure in which two fluorene rings are bonded while crossing each other such as a spirofluorene ring; and the like. Among the rings, the fluorene ring and the spirofluorene ring are preferable.

In the photoelectric conversion element, in order to achieve a high external quantum efficiency and a low dark current, it is preferable to use a material which forms an amorphous film. The reason is because when there is a crystal grain boundary in the film, the crystal grain boundary becomes a carrier trap, and leads to a lowering of the photoelectric conversion efficiency and an increase in the dark current. In addition, in the case of an organic compound layer which contacts an electrode, for example, like an electron blocking layer and a hole blocking layer, it is preferable that the organic compound layer is particularly an amorphous thin film. The aggregation state accompanying the crystal phase loses the uniformity of the film quality, and sometimes an electric field locally concentrates. Such a local electric-field concentration causes an in-plane dispersion of a leakage current and sensitivity, and as a result, lowers the stability of the element characteristics.

As described above, the organic compound of the present embodiment is a material that tends to easily form the amorphous thin film, and accordingly can be suitably used as a constituent material of the photoelectric conversion element.

(2) High Thermal Stability

The glass transition temperature is used as an index of the thermal stability of the organic compound layer in the photoelectric conversion element. In a thin film formed from an organic compound, in general, when the temperature exceeds the glass transition temperature, the molecules cause thermal motion such as rotation and vibration, which results in impairing the stability of the film, and accordingly it is preferable that the thin film has a higher glass transition temperature. Considering the case where the photoelectric conversion element is used as a photo sensor, the thermal stability against a high-temperature process is required which is typified by a mounting process such as a color filter process and a wire bonding process. In particular, the organic compound layer coming into contact with the electrode results in being directly affected by external heat, and accordingly is required to have higher thermal stability.

As a result of the study of the present embodiment by the present inventors, it has been found that in order to raise the glass transition temperature, it is effective to increase the molecular weight, to make the molecular shape to have a demolished symmetry, to introduce a bulky alkyl group, and to reduce the rotation axis. Accordingly, for example, by introduction of aryl groups into substitution positions of $R_1$, $R_2$, $R_7$ and $R_8$ in the general formula [1], as in the Exemplary Compound A1, the glass transition temperature can be raised. In addition, by the introduction of a bulky alkyl group such as a tert-butyl group into the indole skeleton or a substituent which substitutes the indole skeleton, the glass transition temperature can be raised.

As described above, the organic compound of the present embodiment can form the amorphous thin film having higher thermal stability, by controlling the basic structure including the indole skeleton so as to increase the molecular weight, form a molecular shape of which the symmetry is demolished, introduce a bulky alkyl group thereinto, and reduce the rotation axes. Because of this, the organic compound of the present embodiment can be suitably used as the constituent material of the photoelectric conversion element.

(3) Wide Band-Gap Performance

In the photoelectric conversion element, in order that a high external quantum efficiency is achieved, it becomes necessary that more light reaches the photoelectric conversion layer. For example, when the electron blocking layer positioned in the light incidence direction has absorption in the visible light region, the light reaching the photoelectric conversion layer decreases and the external quantum efficiency results in decreasing. In other words, a material having little absorption in the visible light region is preferable as the electron blocking layer. On the other hand, in order that the electron blocking layer sufficiently suppresses the injection of electrons from the electrode, it is preferable that the film thickness of the layer is thicker. When the film thickness is not sufficiently thick, there is a possibility that tunnel type electron injection occurs when the voltage is applied; and that unevenness and foreign substances on the electrode surface cannot be sufficiently covered, and accordingly a physical short circuit and a leakage current are caused. In addition, when the film is thin, the film resists becoming uniform, and the photoelectric conversion layer and the electrode result in locally approaching each other. Then, there is a possibility that an electric field concentrates in the proximity portion, and electric charges are injected from the electrode. Accordingly, a material that constitutes the charge blocking layer is preferably a material which shows little absorption in the visible light region even if the film is sufficiently thickened and does not reduce light reaching the photoelectric conversion layer.

<Comparison between Exemplary Compounds A1 and B1 of Present Embodiment and Comparative Compound b-1>

Exemplary Compounds A1 and B1 of the present embodiment are represented by the following structural formulae.

A1

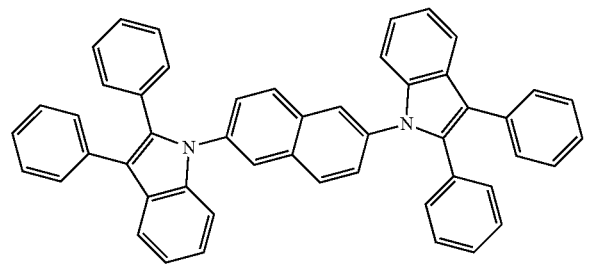

-continued

B1

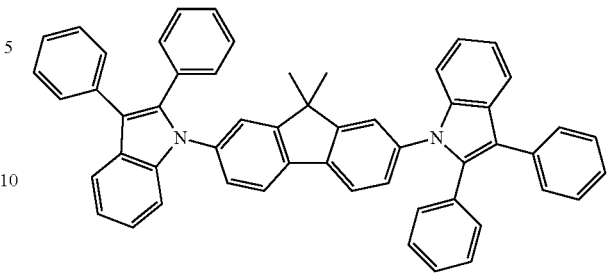

Comparative compound b-1 is represented by the following structural formula.

b-1

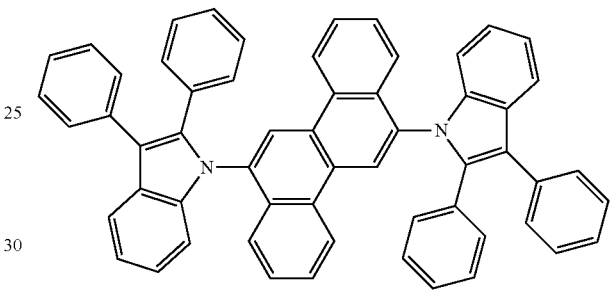

The Exemplary Compounds A1 and B1 of the present embodiment and the comparative compound b-1 will be compared from the viewpoint of absorption characteristics. Table 1 shows results of S1 and LUMO which have been calculated by calculation using a molecular orbital method, in the Exemplary Compounds A1 and B1 of the present embodiment and the comparative compound b-1. It is found that S1 of each of the Exemplary Compounds A1 and B1 of the present embodiment shows a shorter wavelength than that of the comparative compound b-1. This reason is because the spacers in the Exemplary Compounds A1 and B1 of the present embodiment have fused aromatic rings which have each a smaller number of carbon atoms than that of the fused aromatic ring of the spacer in the comparative compound b-1. In other words, it is preferable that the organic compound of the present embodiment uses a fused aromatic ring having a low effect of expanding the conjugation, for a spacer.

In addition, in the present embodiment, the visible light region is 420 nm or longer and 700 nm or shorter. When the S1s in Table 1 are compared, it is understood that the comparative compound b-1 has S1 of 420 nm or longer and has an absorption in the visible light region, but the Exemplary Compounds A1 and B1 of the present embodiment have S1 shorter than 420 nm and do not have the absorption in the visible light region. An optical band gap of a vapor-deposited film of the Exemplary Compound A1 of the present embodiment was actually calculated from the absorption end of the absorption spectrum, and as a result, the optical band gap was 386 nm; and thus it was confirmed that the Exemplary Compound A1 had no absorption in the visible light region.

TABLE 1

| | S1/nm (calculated value) | LUMO/eV |
|---|---|---|
| 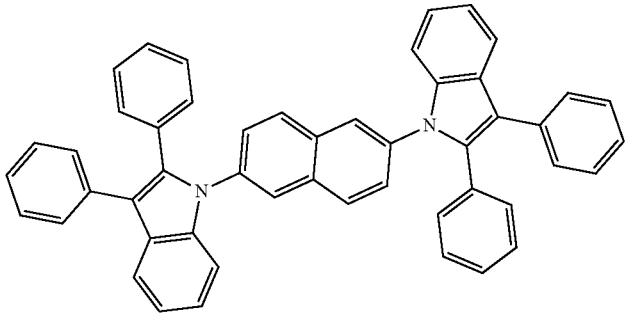 [SMILES: c1ccc(-c2c(-c3ccccc3)n(-c3ccc4cc(-n5c(-c6ccccc6)c(-c6ccccc6)c6ccccc65)ccc4c3)c3ccccc23)cc1]<br>A1 | 393 | −1.50 |
| 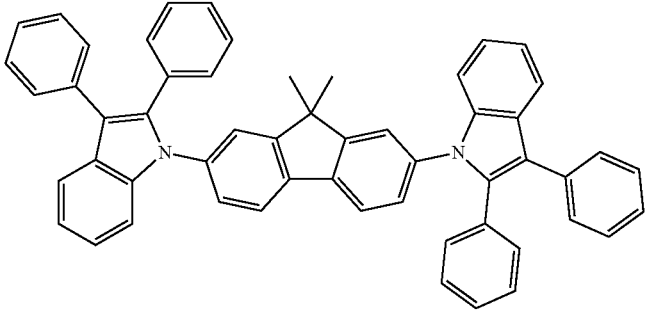 [SMILES: CC1(C)c2cc(-n3c(-c4ccccc4)c(-c4ccccc4)c4ccccc43)ccc2-c2ccc(-n3c(-c4ccccc4)c(-c4ccccc4)c4ccccc43)cc21]<br>B1 | 367 | −1.26 |
| 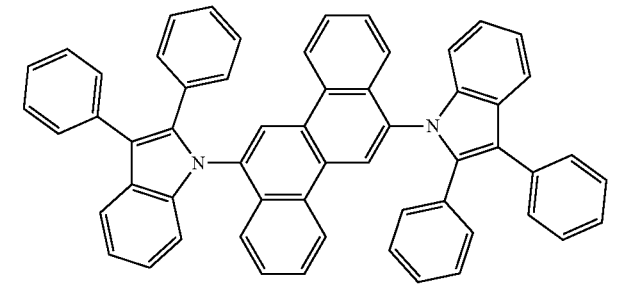 [SMILES: c1ccc(-c2c(-c3ccccc3)n(-c3cc4c5ccccc5c(-n5c(-c6ccccc6)c(-c6ccccc6)c6ccccc65)cc4c4ccccc34)c3ccccc23)cc1]<br>b-1 | 425 | −1.73 |

As seen above, the case in which the spacer A is naphthalene or fluorene has been described as an example, but the case in which the spacer A is another specified group is also similar. Therefore, the organic compound of the present embodiment has a wide band gap (S1) and does not have absorption in the visible light region, and accordingly can be suitably used as the constituent material of the photoelectric conversion element. It is particularly preferable to use the organic compound as a layer which comes into contact with the electrode. Incidentally, as for a measuring method of the absorption spectrum, V-560 made by JASCO Corporation was used as a measuring apparatus. A vapor-deposited film sample having the organic compound vapor-deposited on a quartz substrate at a degree of vacuum of $5\times10^{-4}$ Pa or lower was used for measurement.

As for a calculation technique of calculation by the molecular orbital method, the density functional formalism (Density Functional Theory, DFT) was used which is widely used at present. B3LYP was used as a general-purpose function, and 6-31G* was used as a default function. Incidentally, the molecular orbital calculation was carried out according to Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B.

Foresman, J. V Ortiz, J. Cioslowski, and D. J. Fox, Gaussian, Inc., Wallingford Conn., 2010), which is widely used at present.

(4) High Electron-Blocking Property

In the photoelectric conversion element, in order to suppress the injection of the electric charges from the electrode and reduce the dark current, an injection barrier between the electrode and the charge blocking layer needs to be sufficiently large. For example, in order that the electron blocking layer sufficiently suppresses the injection of electrons from the hole collecting electrode, it is preferable that the LUMO level is shallow (close to the vacuum level). As described above, the organic compound of the present embodiment has a fused aromatic ring or a heteroarylene group which have a comparatively small number of carbon atoms, as the spacer A, and accordingly is a compound which has a wide band gap. Specifically, the energy difference between HOMO and LUMO becomes large, and as a result, the LUMO level becomes shallow (close to the vacuum order). It is also understood from the result of the calculation by the molecular orbital method shown in Table 1 that LUMO of each of the Exemplary Compounds A1 and B1 of the present embodiment is shallower than that of the comparative compound b-1.

As described above, the compound of the present embodiment has high electron-blocking capability and can be suitably used as the electron blocking layer of the photoelectric conversion element.

(5) High Hole-Transporting Performance

In the photoelectric conversion element, in order that a high external quantum efficiency is achieved, it becomes necessary that the electric charges generated in the photoelectric conversion layer are promptly transported to the collecting electrode. For example, holes generated in the photoelectric conversion layer reach the hole collecting electrode through the electron blocking layer. On the other hand, as described above, the electron blocking layer is preferably a thick film in order to sufficiently suppress the injection of electrons from the electrode. Therefore, it is preferable that the electron blocking layer can promptly transport the holes generated in the photoelectric conversion layer to the hole collecting electrode, even though the film is formed sufficiently thick.

The organic compound of the present embodiment has an indole skeleton. Specifically, the organic compound has an indole skeleton excellent in hole transporting capability at both ends, accordingly is a material having high hole transporting capability, and can be suitably used as the electron blocking layer of the photoelectric conversion element.

<<Specific Examples of Organic Compound of Present Embodiment>>

Specific examples of the organic compound of the present embodiment will be described below. However, the organic compound of the present embodiment is not limited to these specific examples.

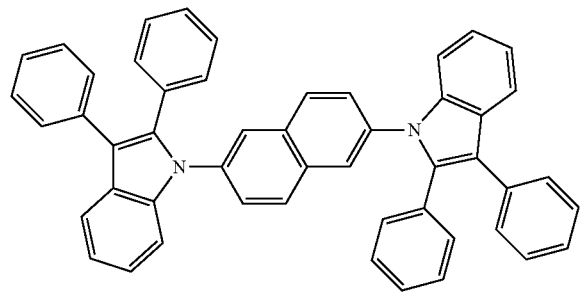

A1

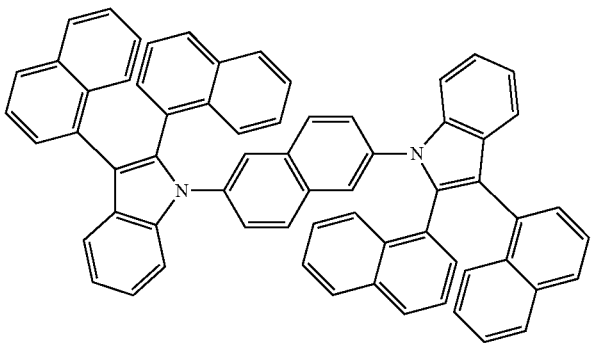

A2

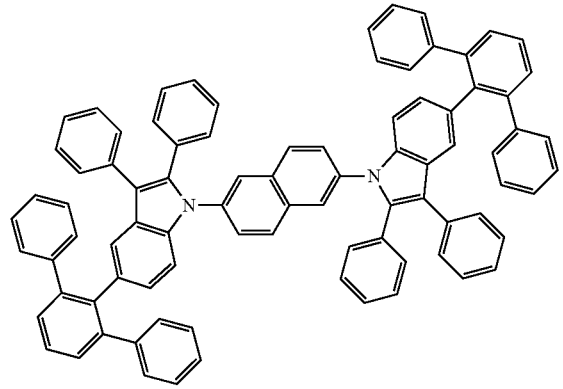

A3

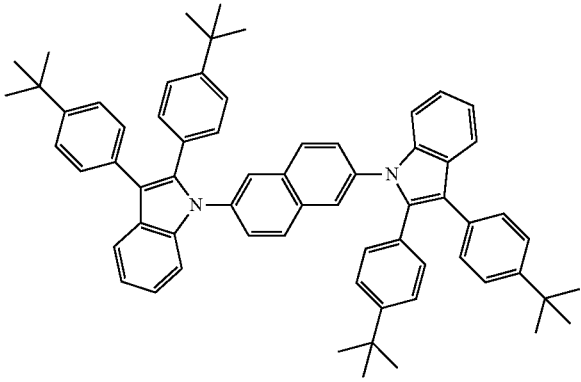

A4

-continued
A5
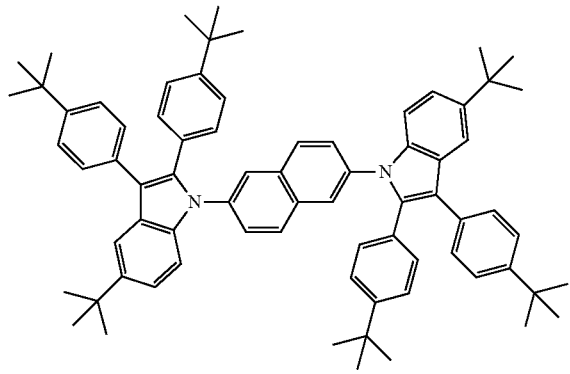
A6
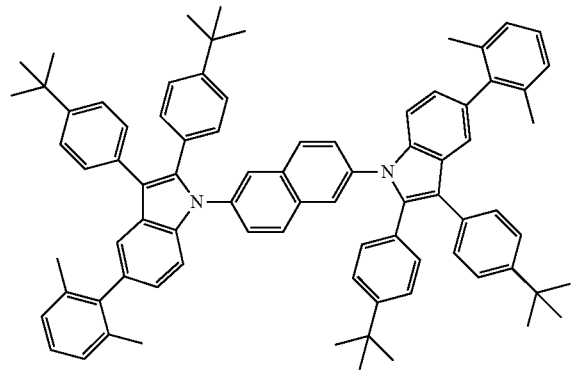
A7
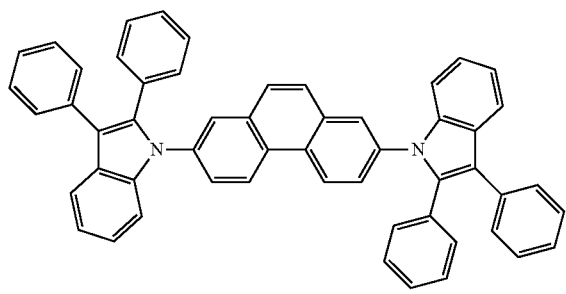
A8
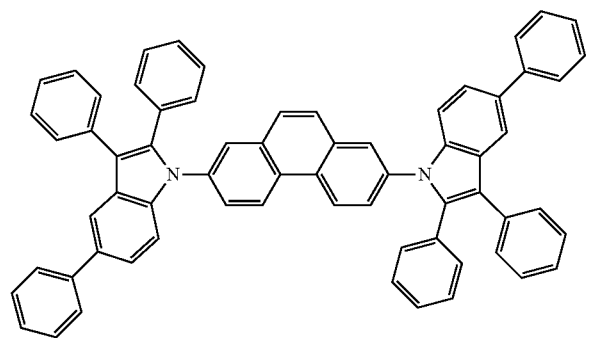
A9
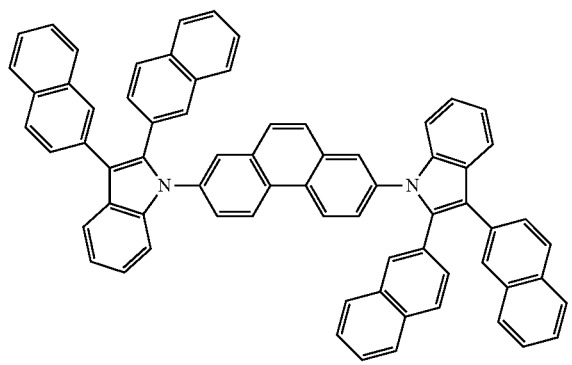
A10
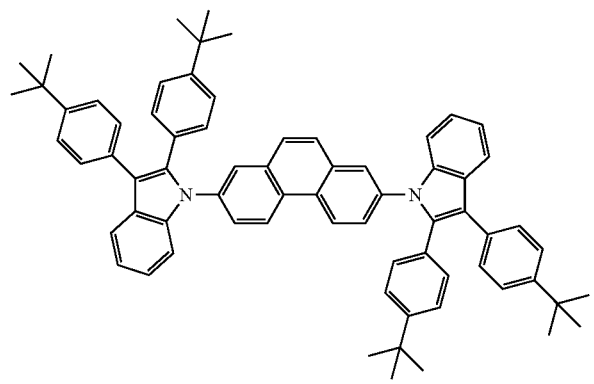

-continued
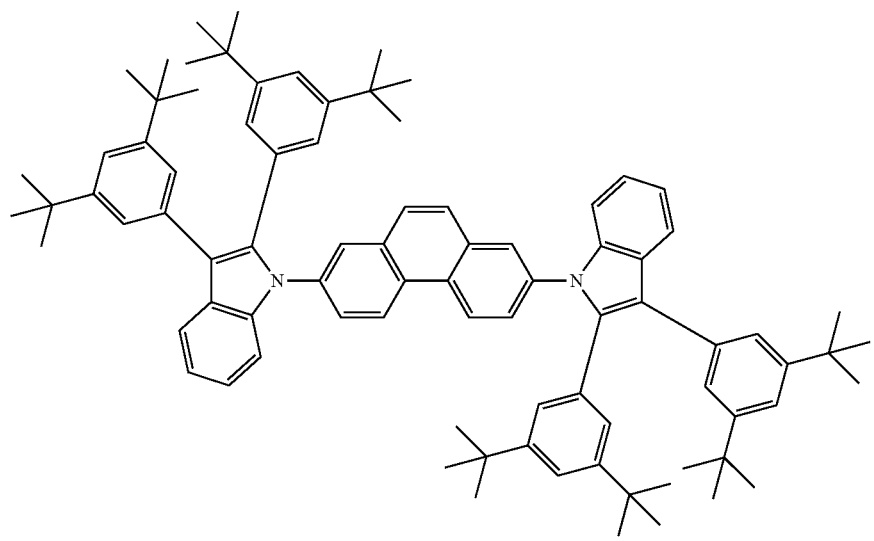
A11
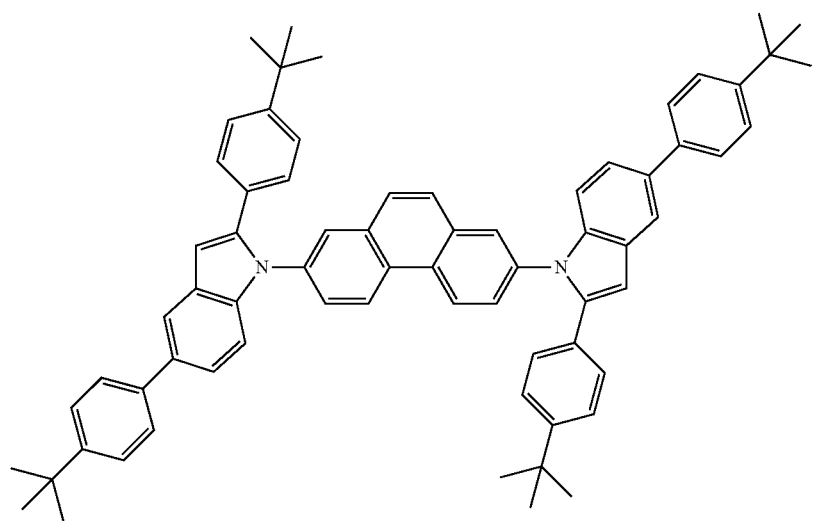
A12
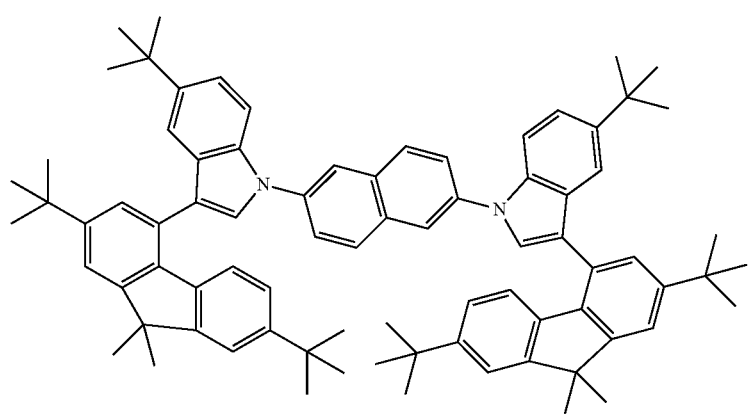
A13

A14
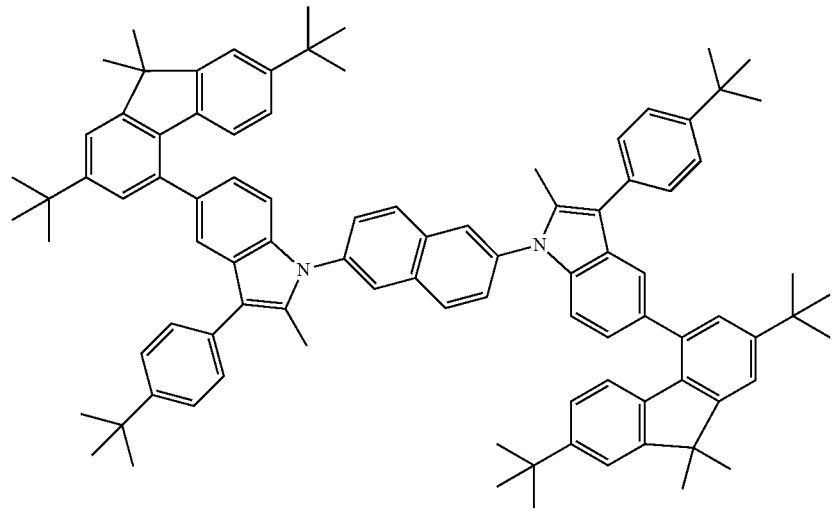
A15
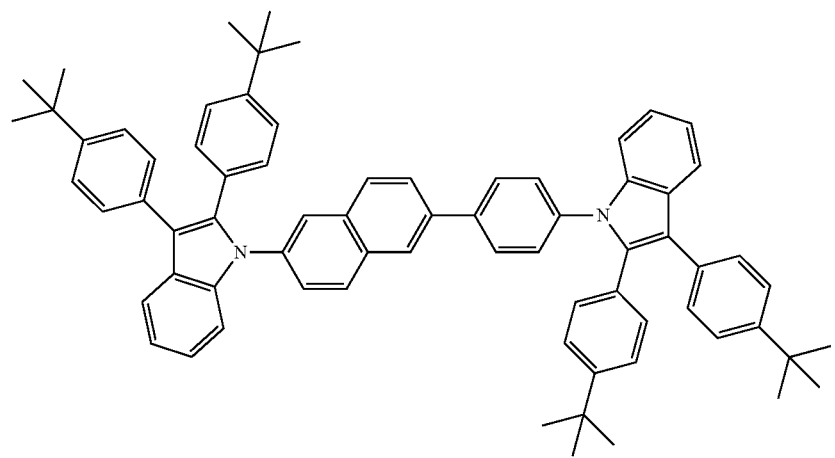
A16
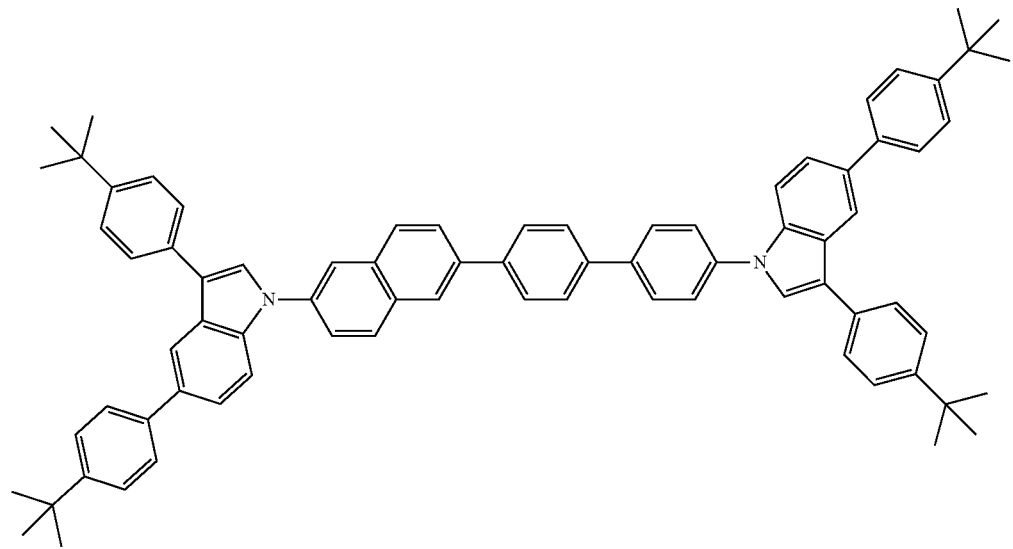

-continued
A17
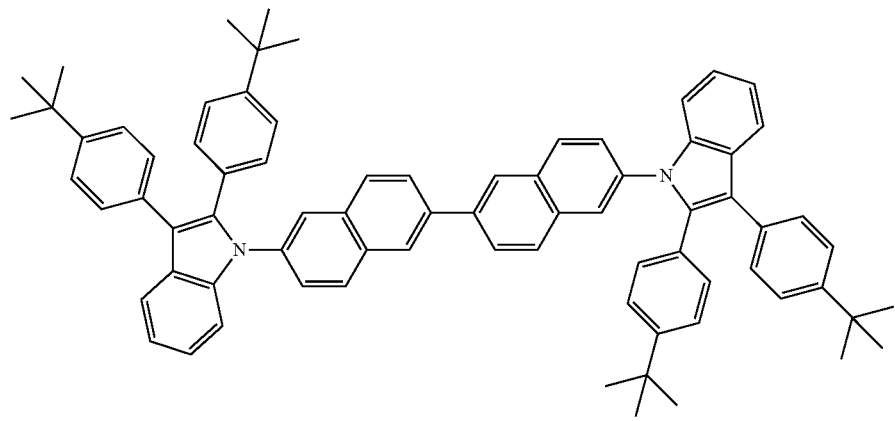
A18
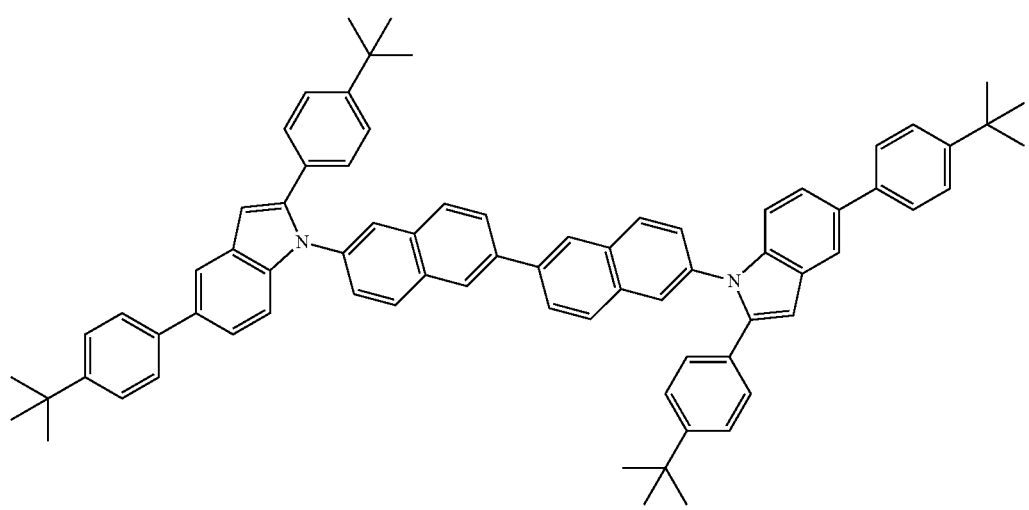
A19
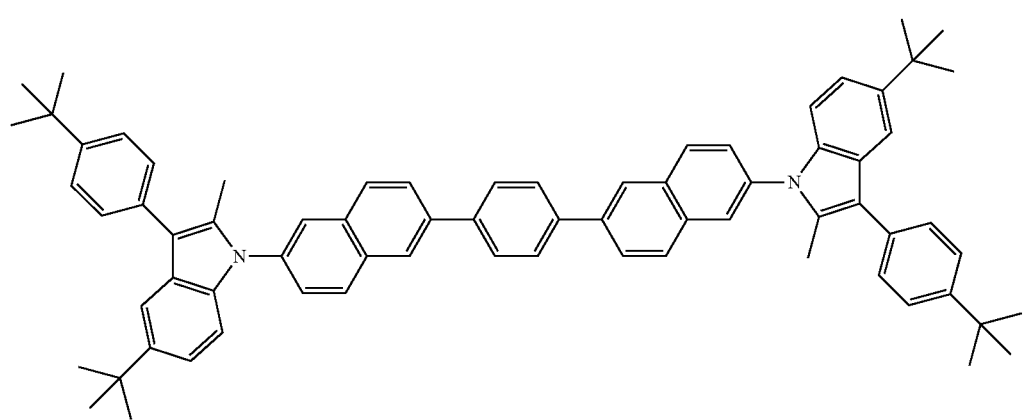

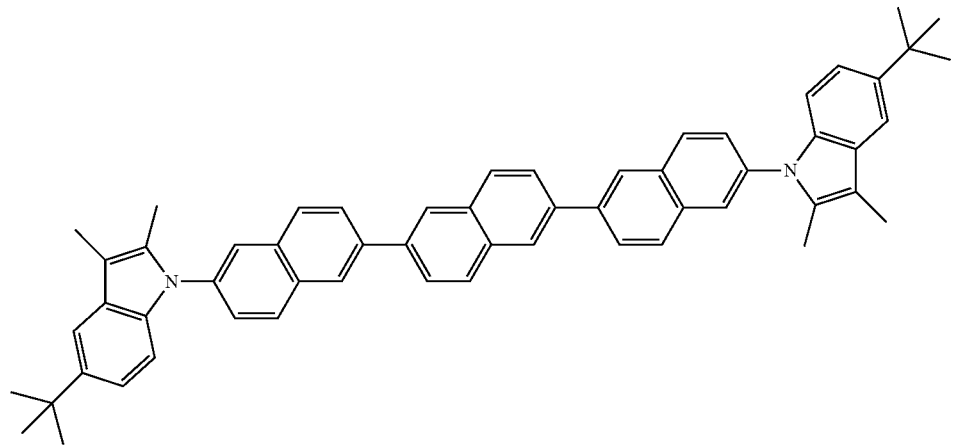
A20
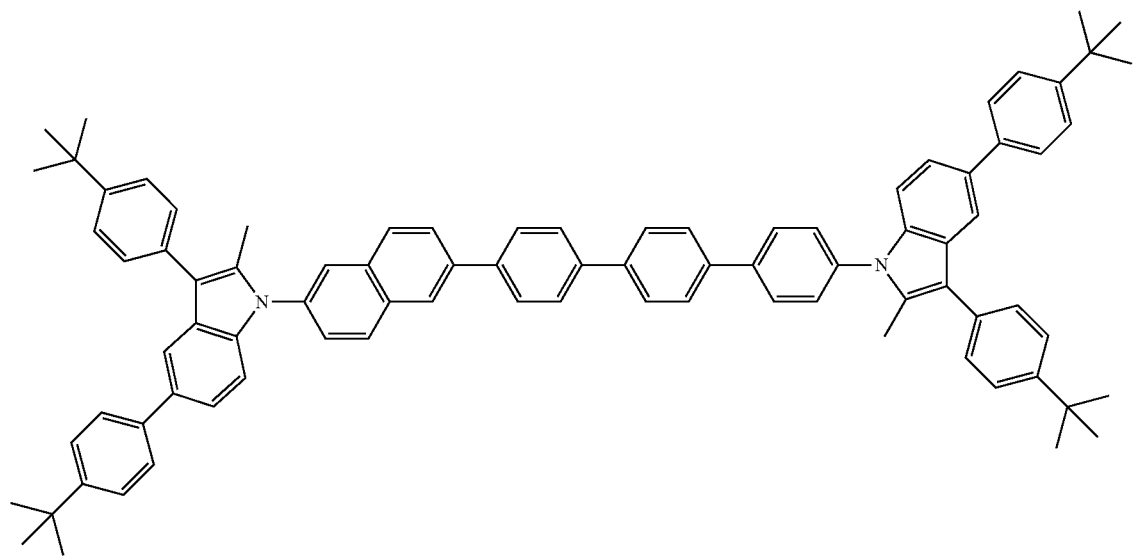
A21
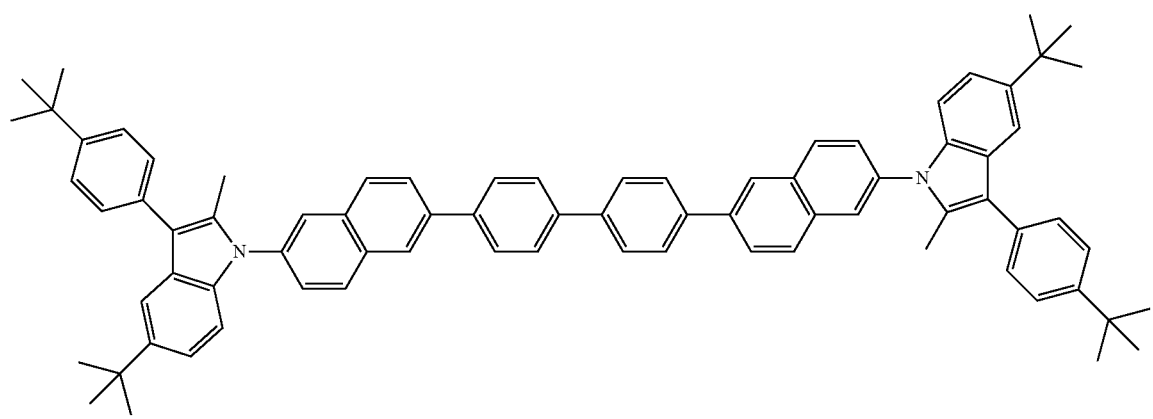
A22

B1 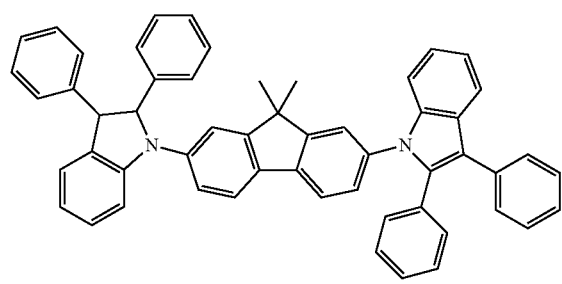
B2 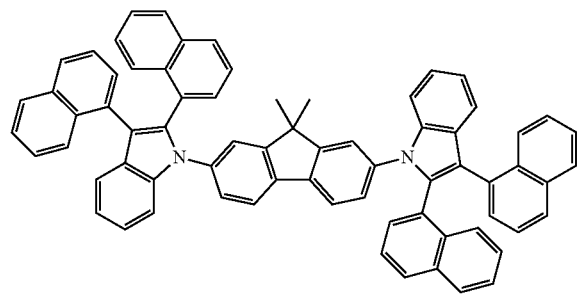
B3 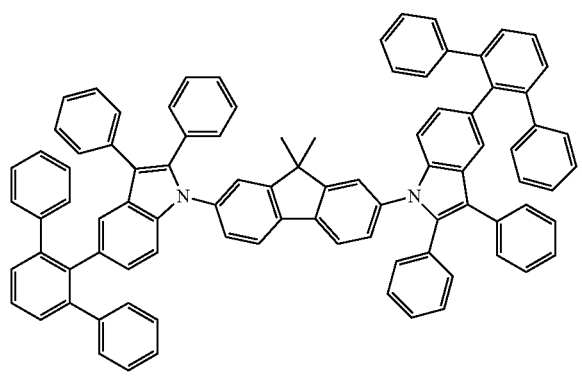
B4 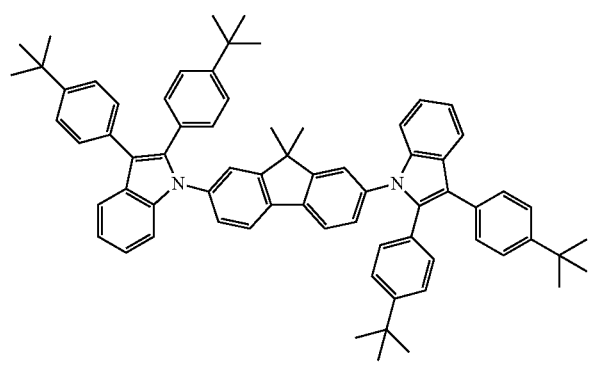
B5 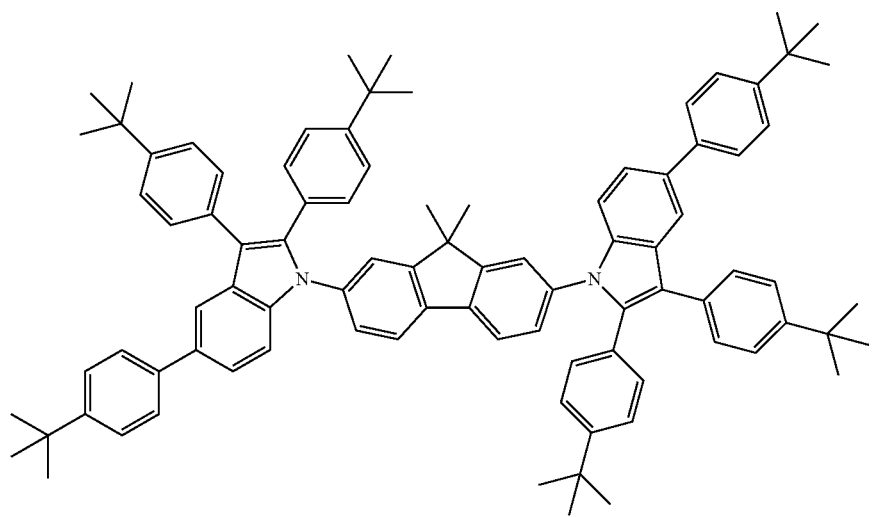

-continued
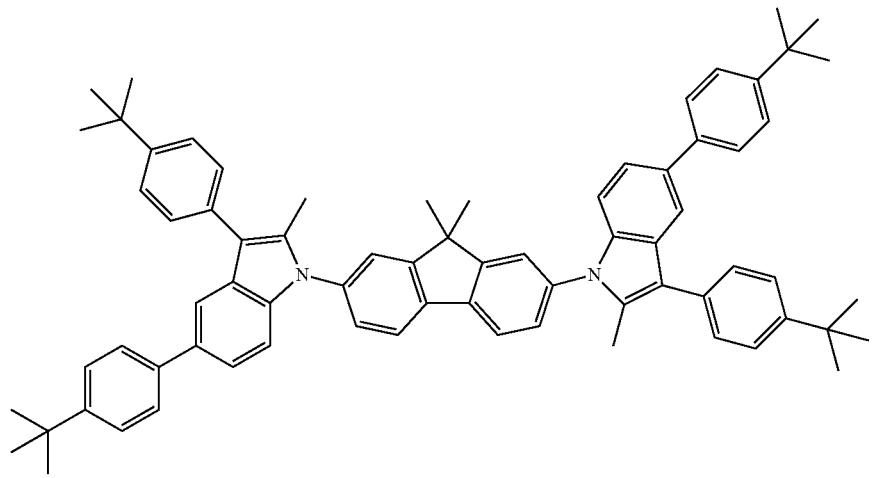
B6
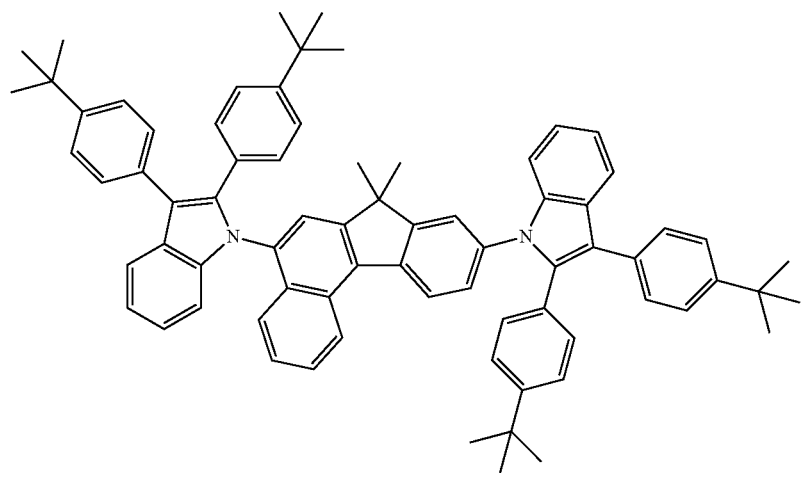
B7
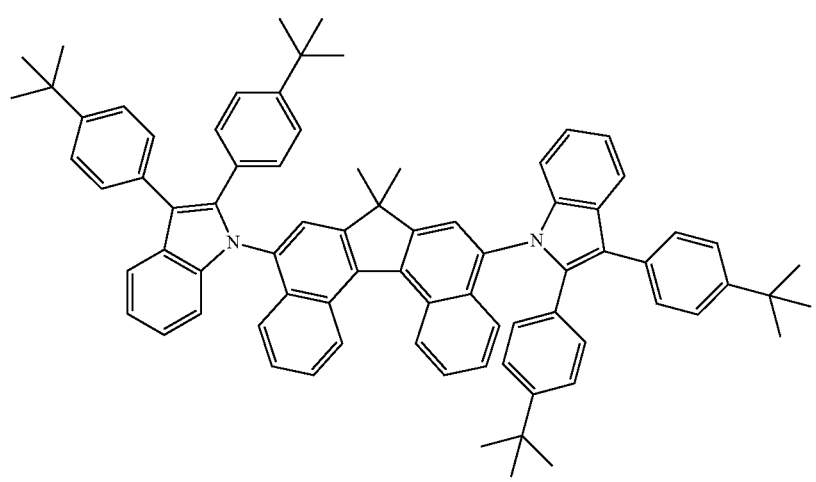
B8

-continued
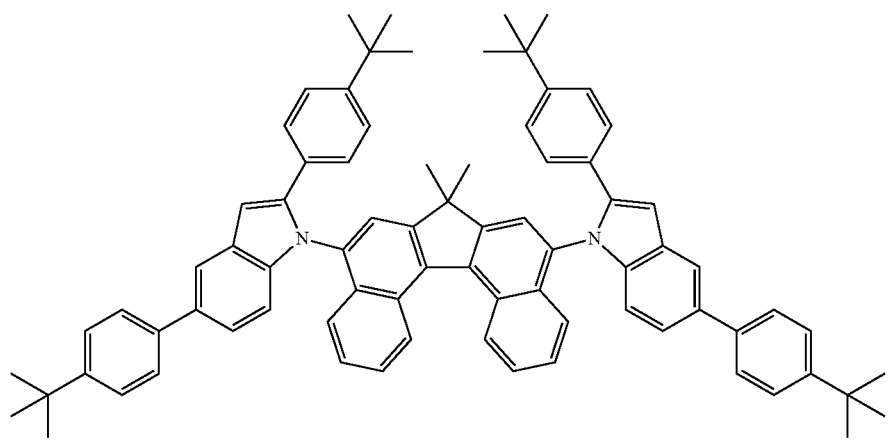
B9
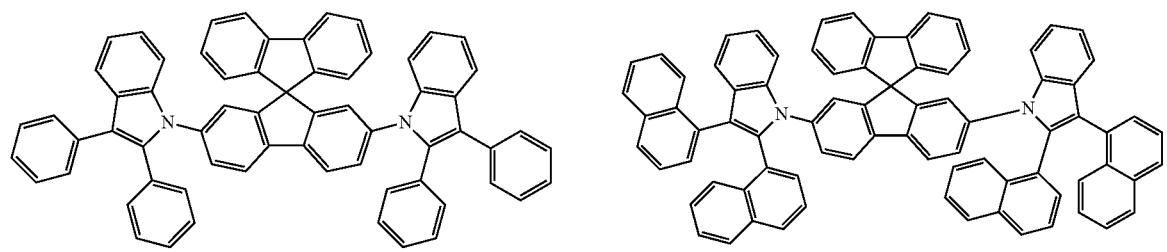
B10    B11
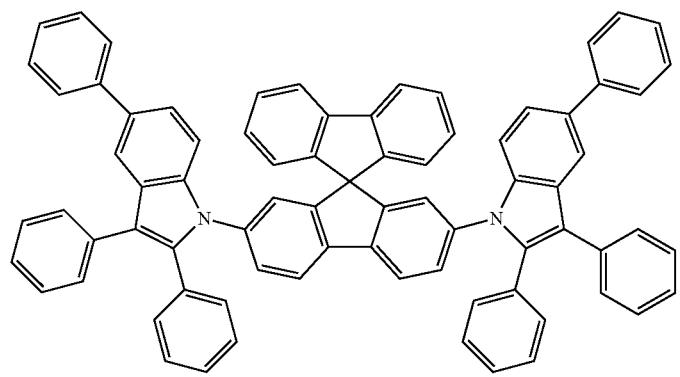
B12
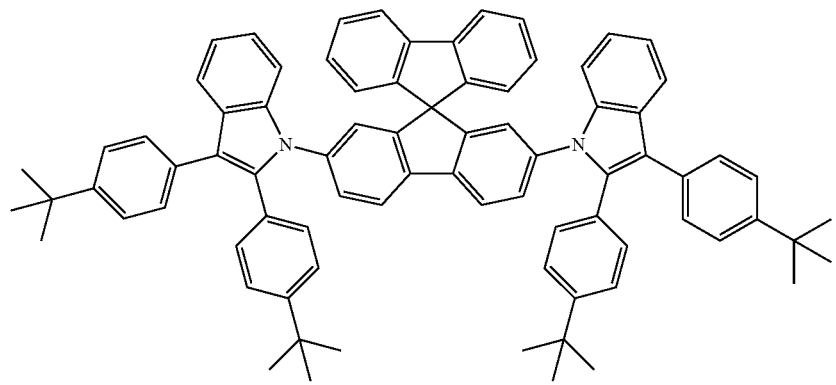
B13

-continued
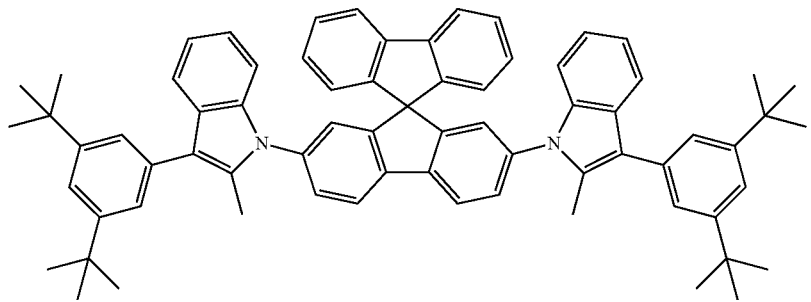
B14
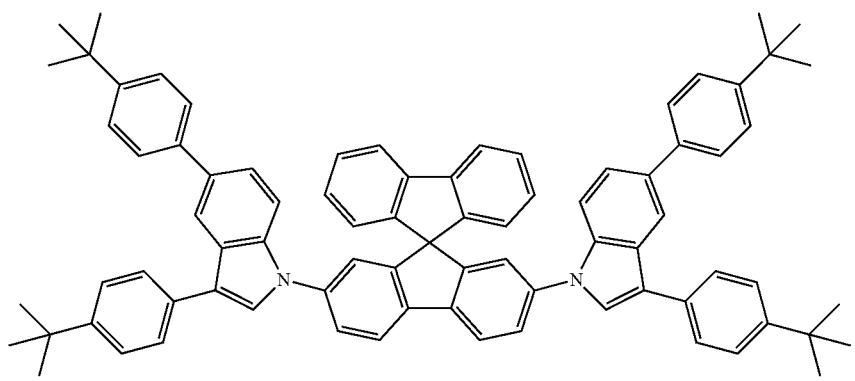
B15
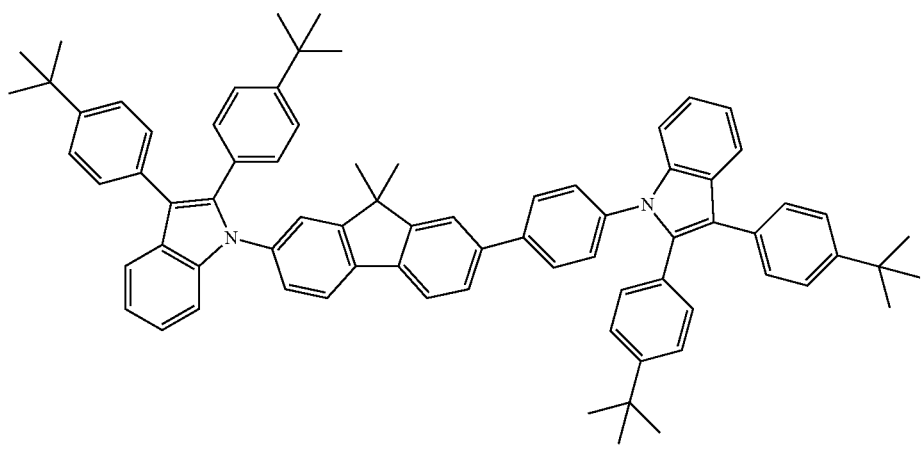
B16
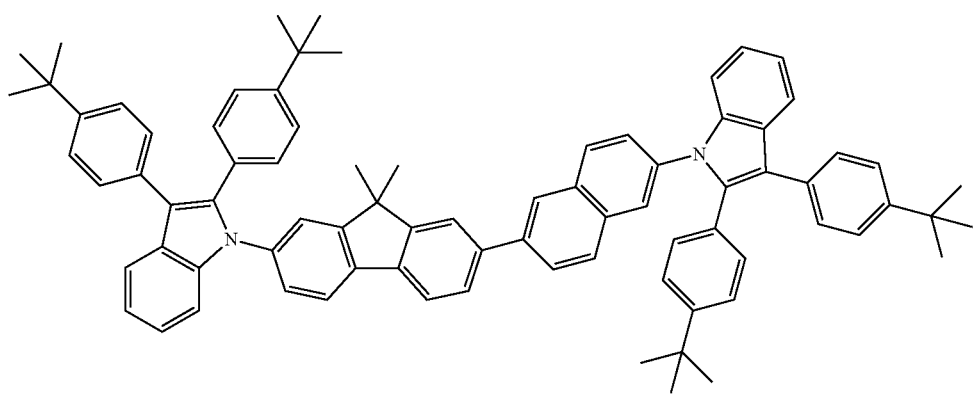
B17

-continued
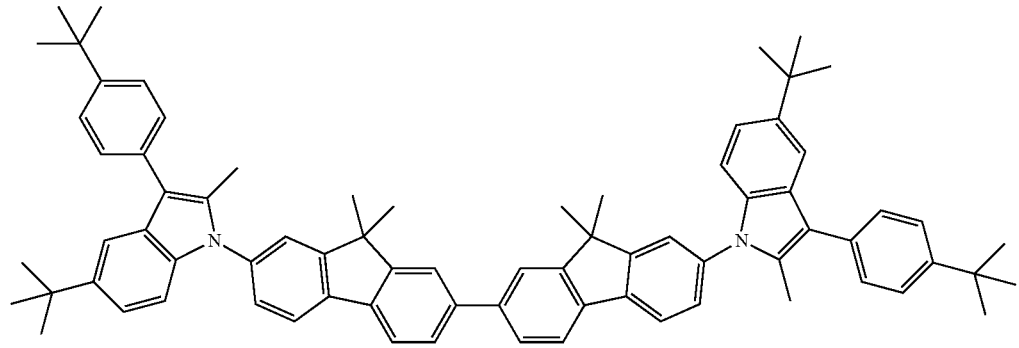
B18
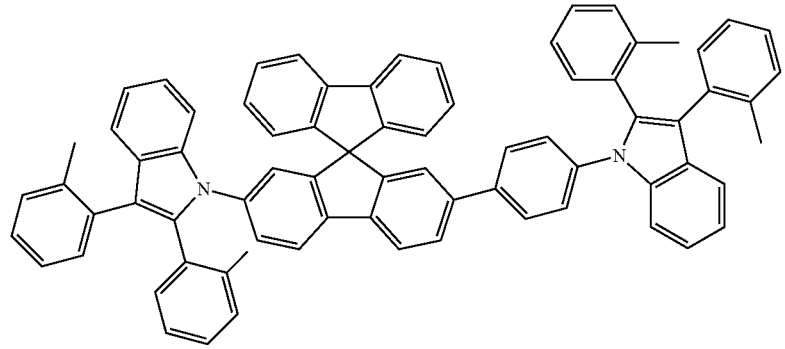
B19
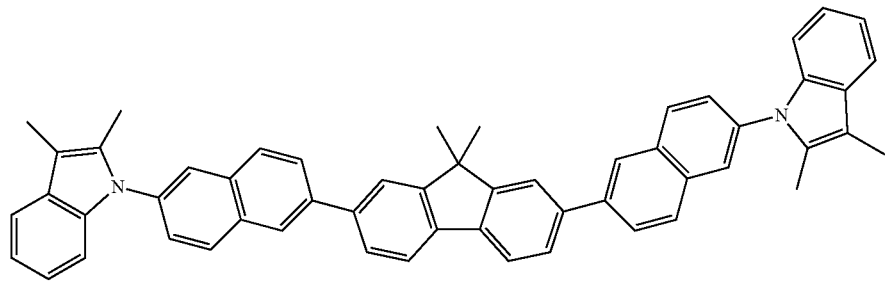
B20
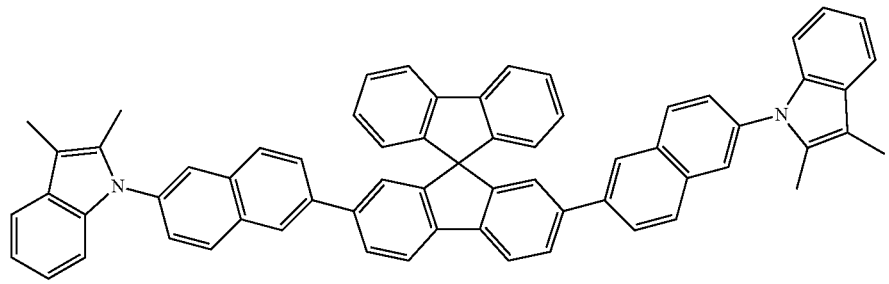
B21
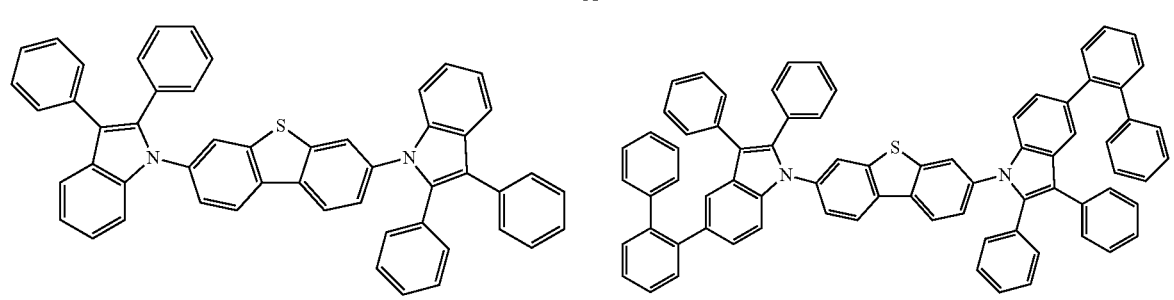
C1  C2

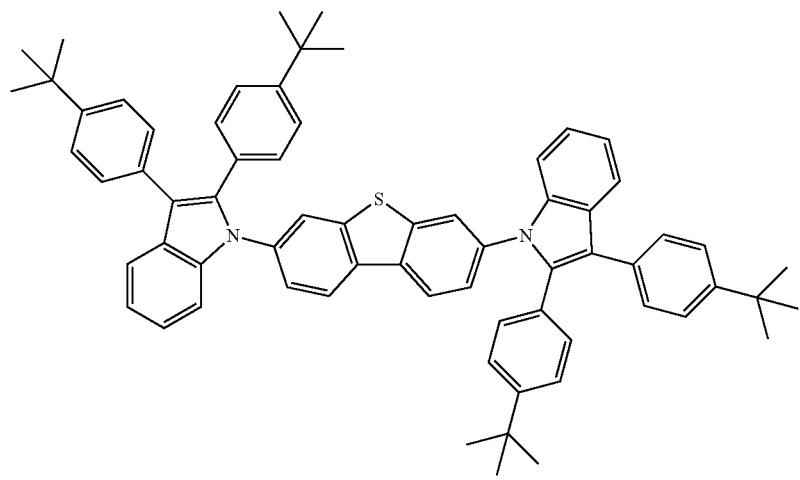
C3
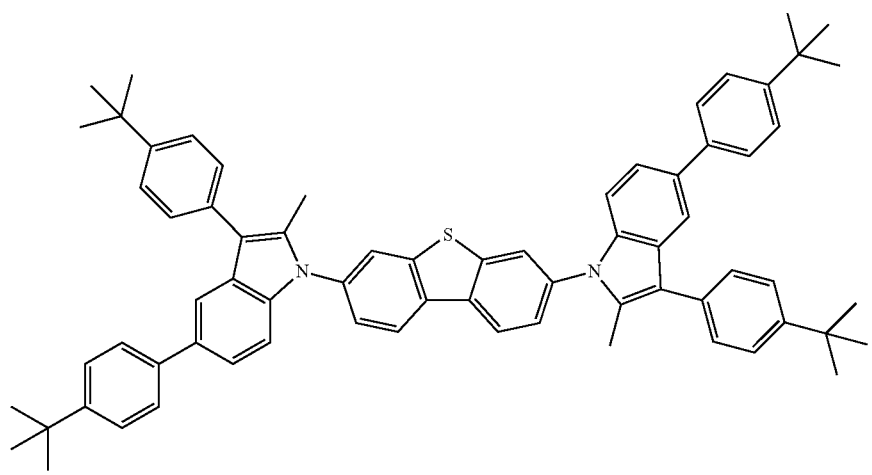
C4
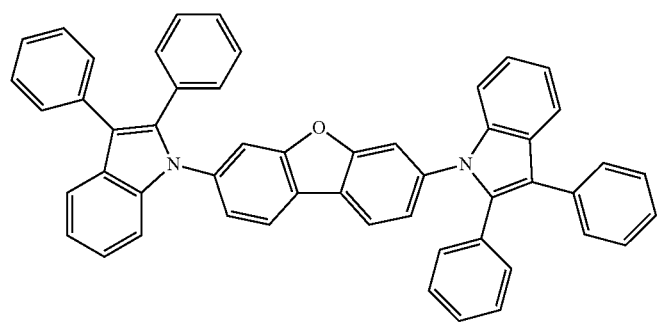
C5

-continued
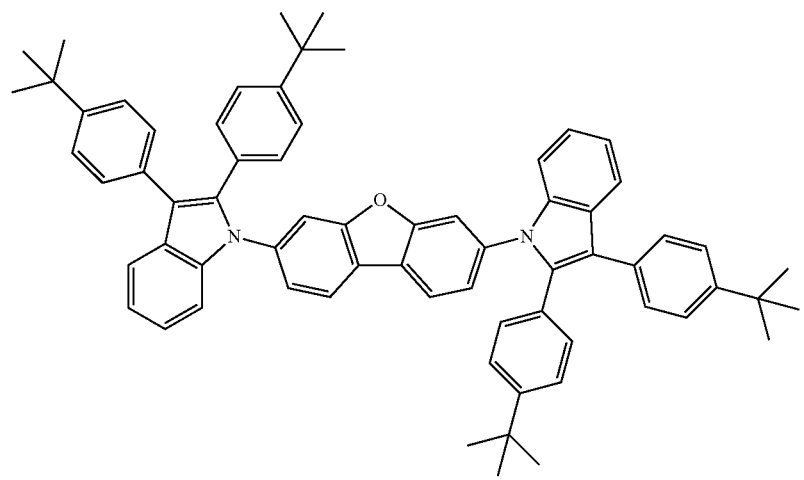
C6
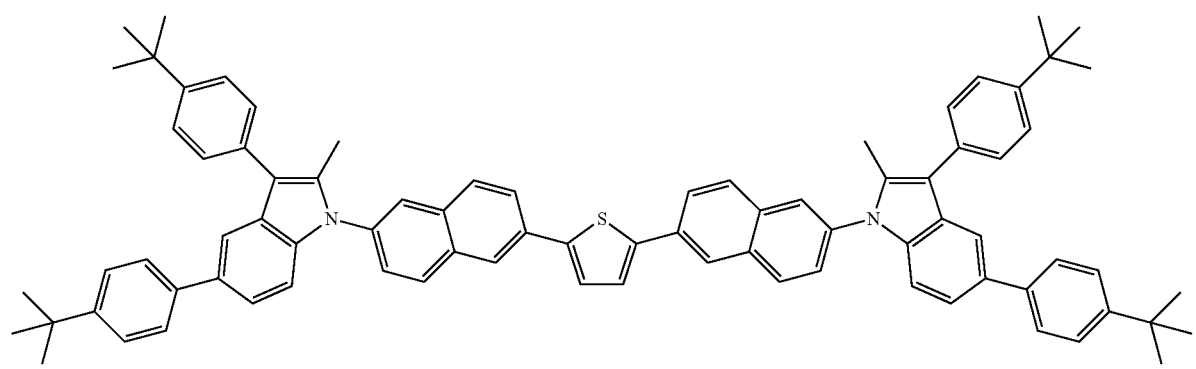
C7
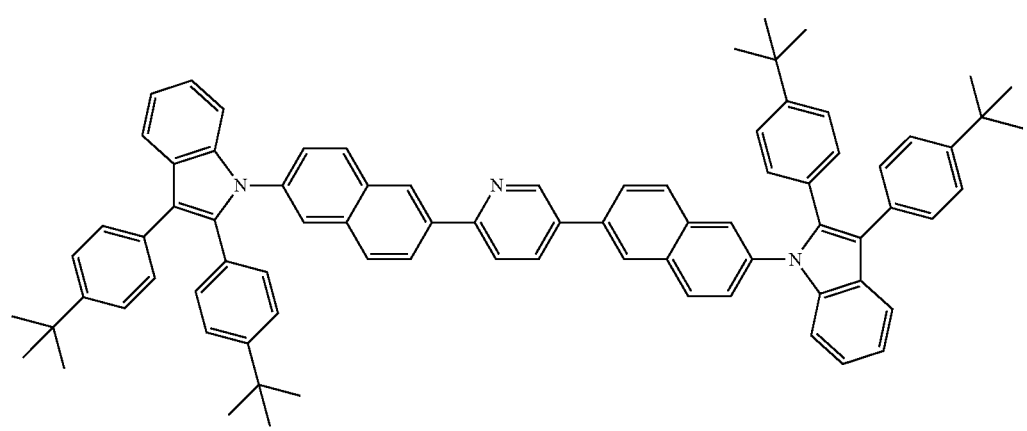
C8

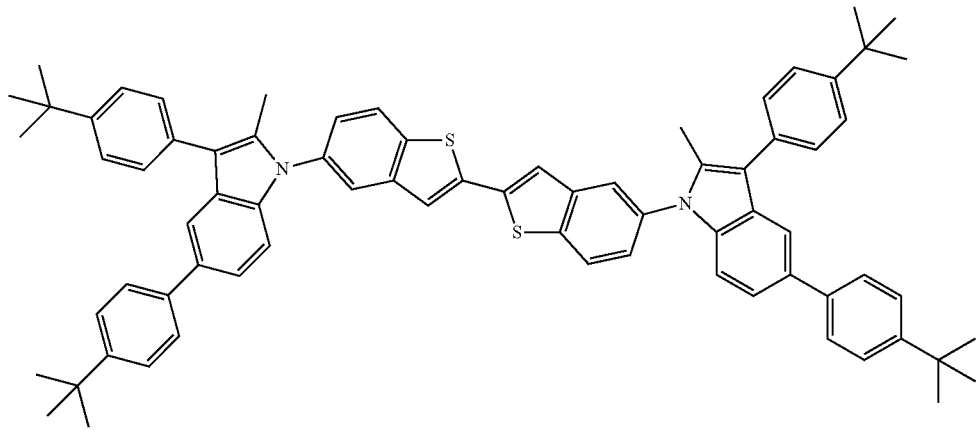

C9

Among the organic compounds of the present embodiment, Group A includes organic compounds of which the spacers A and B in the formula [1] are formed of a benzene ring, a naphthalene ring or a phenanthrene ring which are structures having a high planarity. Among the organic compounds of the present embodiment, the Group A is particularly excellent in point of stability due to an electronic effect and a hole transporting property. Accordingly, the Group A can be used also for the electron blocking layer. For example, when the organic compound of Group A among the organic compounds of the present embodiment is used for the electron blocking layer of the photoelectric conversion element, the organic compound shows an effect of lowering a driving voltage because of having a high hole-transporting property.

Among the organic compounds of the present embodiment, Group B contains a fluorene ring, a benzofluorene ring, a dibenzofluorene ring or a spirofluorene ring which have each a bulky structure, in the spacers A and B in formula [1]. Among the organic compounds of the present embodiment, the Group B is particularly excellent in point of suppressing molecular packing. Specifically, the Group B tends to easily form a stable amorphous thin film. Furthermore, among the Group B, B10 to B15, B19 and B21 which contain the spirofluorene ring are bulky and do not have a rotational site, and accordingly have the high glass transition temperature. In addition, among the organic compounds of the present embodiment, the Group B has an aromatic ring having a small degree of expansion of the conjugation, and accordingly has a wide band gap. Furthermore, the Group B has a high effect of suppressing the molecular packing, and accordingly can maintain the wide band gap even when having formed a thin film. Thereby, the LUMO is shallow (close to the vacuum order). Accordingly, the Group B can be used also for the electron blocking layer. For example, when the organic compound of Group B among the organic compounds of the present embodiment is used for the electron blocking layer of the photoelectric conversion element, the electron blocking layer has a high capability of blocking electrons from the electrode due to the wide band gap and the shallow LUMO, and accordingly shows an effect of suppressing the dark current.

Among the organic compounds of the present embodiment, Group C contains a heteroarylene group having 4 to 12 carbon atoms, in the spacers A and B in formula [1]. The heteroarylene group is excellent particularly in the hole transporting capability, because sulfur atoms and oxygen atoms have many non-shared electron pairs and accordingly an interaction between molecules becomes large. In addition, it is easy to adjust the electron level represented by HOMO-LUMO, to a range different from that in the arylene group. In other words, the Group C is excellent in a point of adjusting the hole transporting property and the HOMO-LUMO level. Accordingly, the Group C can be used also for the electron blocking layer. For example, when an organic compound of the Group C among the organic compounds of the present embodiment is used for the electron blocking layer of the photoelectric conversion element, the organic compound shows an effect of lowering the driving voltage because of having the high hole-transporting property, and shows an effect of enhancing efficiency and suppressing the dark current by adjustment of the HOMO-LUMO level.

In addition, in terms of thermal stability, the organic compound of the Group C has a tert-butyl group which is a bulky substituent, and an aryl group which substitutes at an ortho position, on the end of the molecule, and as the organic compound becomes a structure having a higher molecular weight in a sublimable range, is adequate in point of the glass transition temperature and the thermal stability.

Electronic Element and Photoelectric Conversion Element According to Present Embodiment of Present Invention (1) Electronic Element and Photoelectric Conversion Element An electronic element according to one embodiment of the present invention (hereinafter referred to as "electronic element of present embodiment") includes a pair of electrodes and an organic compound layer that is arranged between the pair of electrodes, wherein the organic compound layer includes a layer that contains an organic compound of the present embodiment. In addition, a photoelectric conversion element according to one embodiment of the present invention (hereinafter referred to as "photoelectric conversion element of present embodiment") is one embodiment of the electronic element of the present embodiment, and includes an anode, a cathode and an organic compound layer that is arranged between the anode and the cathode, wherein the organic compound layer includes a layer that contains an organic compound of the present embodiment. FIG. 1 illustrates a schematic cross-sectional view illustrating one example of a photoelectric conversion element according to the present embodiment. In the photoelectric conversion element 10, the organic compound layer is arranged between the anode 5 and the cathode 4, and the organic compound layer includes a first organic layer 1. The first organic layer 1 is a layer which forms the photoelectric conversion section that converts light into electric charges. From the above reason, the first organic layer 1 can be also referred to as the photoelectric conversion layer. When the photoelectric conversion element 10 has a plurality of layers, it is preferable that the plurality of layers are stacked in the direction from the anode 5 to the cathode 4. The organic compound layer may have a second organic layer 2 that is arranged between the first organic layer 1 and the cathode 4, and a third organic layer 3 that is arranged between the first organic layer 1 and the anode 5. A protective layer 7, a wavelength selecting section 8 and a lens 9 are arranged on the cathode 4. A readout circuit 6 is connected to the anode 5. The photoelectric conversion element 10 may be formed on an unillustrated substrate. When performing photoelectric conversion, the photoelectric conversion element 10 may apply voltage between the anode 5 and the cathode 4. The voltage is preferably approximately 1 V or higher and 15 V or lower, though depending on the total film thickness of the organic compound layer. The voltage is more preferably approximately 2 V or higher and 10 V or lower.

(2) Substrate

The photoelectric conversion element of the present embodiment may have a substrate. Examples of the substrate include a glass substrate, a flexible substrate and a semiconductor substrate.

In addition, the photoelectric conversion element according to the present embodiment may have a semiconductor substrate. The constituent element of the semiconductor substrate is not limited as long as a charge accumulation section and a floating diffusion (FD) can be formed by injection of impurities. Examples thereof include Si, GaAs and GaP. In particular, Si is preferable. The semiconductor substrate may be an N-type epitaxial layer. In the case, a P-type well, an N-type well, a P-type semiconductor region and an N-type semiconductor region are arranged in the semiconductor substrate.

The charge accumulation section is an N-type semiconductor region or a P-type semiconductor region which is formed on the semiconductor substrate by ion implantation, and is a region for accumulating electric charges therein which have been generated in the photoelectric conversion section. In the case where electrons are accumulated, the N-type semiconductor region may be formed on the surface of the semiconductor substrate, or a diode for accumulation, which has a PN structure, may be formed from the substrate surface. In any case, electrons can be accumulated in the N-type semiconductor region. On the other hand, in the case where holes are accumulated, a P-type semiconductor region may be formed on the semiconductor substrate, or a diode for accumulation, which has an NP structure, may be formed from the substrate surface. In any case, holes can be accumulated in the P-type semiconductor region.

The accumulated electric charges are transferred from the charge accumulation section to the FD. This transfer of the electric charge may be controlled by a gate electrode. Electric charges generated in the first organic layer 1 are accumulated in the charge accumulation section, and the electric charges accumulated in the charge accumulation section are transferred to the FD. After that, the electric charges are converted into an electric current by an amplifying transistor (FIG. 2) which will be described later. In addition, when the charge accumulation section forms a PN junction, photoelectric conversion may be performed by the light which has leaked from the above described photoelectric conversion section. The photoelectric conversion element may have a charge output section without having the charge accumulation section. In the case where the photoelectric conversion element has the output section, the electric charges are transmitted from the electrode to an amplifying transistor or the like, without through the FD.

(3) Anode (Electron Collecting Electrode) 5 and Cathode (Hole Collecting Electrode) 4

The anode 5 is an electrode which collects electrons among electric charges generated in the first organic layer 1. In the case of the structure of the imaging device, the anode 5 may be a pixel electrode. The anode 5 may be arranged closer to a pixel circuit side than the cathode 4. The anode 5 can be referred to as an electron collecting electrode, because of its function. Examples of the constituent material of the anode 5 include ITO, indium zinc oxide, $SnO_2$, ATO (antimony doped tin oxide), ZnO, AZO (Al doped zinc oxide), GZO (gallium doped zinc oxide), $TiO_2$ and FTO (fluorine doped tin oxide).

The cathode 4 is an electrode which collects holes among the electric charges generated in the first organic layer 1. In the case of the structure of the imaging device, the electrode may be a pixel electrode. Examples of the constituent material of the cathode 4 include a metal, a metal oxide, a metal nitride, a metal boride, an organic electroconductive compound, and mixtures obtained by combining a plurality of these compounds with each other. Specific examples thereof include: electroconductive metal oxides such as tin oxide (ATO, FTO) doped with antimony, fluorine or the like, tin oxide, zinc oxide, indium oxide, indium tin oxide (ITO) and zinc indium oxide; metal materials such as gold, silver, magnesium, chromium, nickel, titanium, tungsten and aluminum; electroconductive compounds such as oxides, nitrides and the like of these metal materials (for example, titanium nitride (TiN)); furthermore, mixtures or laminates of these metals and these electroconductive metal oxides; inorganic electroconductive substances such as copper iodide and copper sulfide; organic electroconductive materials such as polyaniline, polythiophene and polypyrrole; and laminates of these materials and ITO or titanium nitride. Particularly preferable constituent materials of the cathode 4 are materials selected from the group consisting of an alloy of magnesium and silver, titanium nitride, molybdenum nitride, tantalum nitride and tungsten nitride.

The pixel electrode may be any one of the anode 5 and the cathode 4. It is preferable that an electrode on a light extraction side has high transparency. Specifically, the transparency is 80% or higher. In addition, an electrode on a light incident side can be also referred to as an upper electrode. In the case, the other is referred to as a lower electrode.

A method for forming the above described two types of electrodes (anode and cathode) can be appropriately selected in consideration of suitability to the respective electrode materials to be used. Specifically, the electrodes can be formed by: a wet method such as a printing method and a coating method; a physical method such as a vacuum deposition method, a sputtering method and an ion plating method; a chemical method such as a CVD method and a plasma CVD method; or the like. When the electrode is formed with the use of ITO, the electrode can be formed by a method such as an electron beam method, a sputtering method, a resistance heating vapor-deposition method, a chemical reaction method (sol-gel method or the like) and a coating method of a dispersion of indium tin oxide. In addition, in such a case, the surface of the formed electrode (ITO electrode) may be subjected to UV-ozone treatment, plasma treatment or the like. When the electrode is formed with the use of TiN, various film forming methods can be used which include a reactive sputtering method. In addition, in such a case, the formed electrode (TiN electrode) may be subjected to annealing treatment, UV-ozone treatment, plasma treatment or the like.

(4) First Organic Layer (Photoelectric Conversion Layer) 1

The first organic layer 1 can be also referred to as the photoelectric conversion layer, as described above. The constituent material of the first organic layer 1 of the photoelectric conversion element according to the embodiment will be described below. It is preferable for the first organic layer 1 to show a high light-absorption rate and to efficiently separate received light into the electric charges, in other words, to show high photoelectric conversion efficiency. It is also preferable for the first organic layer 1 to be capable of promptly transporting the generated electric charges, specifically, electrons and holes, to the electrode. In addition, in order to suppress the lowering of the film quality such as crystallization, a material having a high glass transition temperature is preferable. The first organic layer may be a mixed layer with a material having the high glass transition temperature, from the viewpoint of improving the film quality. The first organic layer 1 may have a plurality of types of organic compounds. When the first organic layer 1 contains the plurality of types of organic compounds, the plurality of types of organic compounds may be mixed in one layer, or the plurality of types of organic compounds may be contained in a plurality of layers.

The first organic layer 1 is preferably a layer which contains an organic p-type compound such as a p-type organic semiconductor, or an organic n-type compound such as an n-type organic semiconductor, and is more preferably a layer which contains a bulk hetero layer (mixed layer) in which the organic p-type compound and the organic n-type compound are mixed, at least in a part of itself. By having the bulk hetero layer, the first organic layer 1 can improve the photoelectric conversion efficiency (sensitivity). By having the bulk hetero layer at the optimal mixing ratio, the first organic layer 1 can enhance the electron mobility and the hole mobility of the first organic layer 1, and can increase the photoresponsive speed of the photoelectric conversion element.

It is preferable that the first organic layer 1 contains fullerene, a fullerene analogue or a fullerene derivative, as the n-type organic semiconductor. Hereafter, the fullerene, the fullerene analog and the fullerene derivative may be collectively referred to as "fullerenes" in some cases. An electron path is formed by the plurality of fullerene molecules, and accordingly the electron transporting property is improved and the responsiveness of the photoelectric conversion element is improved. The content of the fullerenes is preferably 20 mass % or more and 80 mass % or less, when the total amount of the photoelectric conversion layer is set at 100%. The fullerene or the fullerene analog is a generic term for clusters which are formed of only a large number of carbon atoms that form a closed-shell hollow shape, and includes C60, and C70, C74, C76 and C78 which are higher order fullerenes. These materials may be used solely or in combination with other one or more types. Materials to be used for charge separation and transportation of electrons are not only the fullerenes. A plurality of other materials may be simultaneously used as the materials. Examples of materials other than the fullerenes include: naphthalene compounds such as known NTCDI which is an n-type organic semiconductor; perylene compounds such as PTCDI; phthalocyanine compounds such as SubPc; and thiophene compounds such as DCV3T.

Examples of the fullerene or the fullerene analogues include fullerene C60, fullerene C70, fullerene C76, fullerene C78, fullerene C80, fullerene C82, fullerene C84, fullerene C90, fullerene C96, fullerene C240, fullerene 540, mixed fullerene and fullerene nanotubes. Examples of the fullerene derivative include the following compounds.

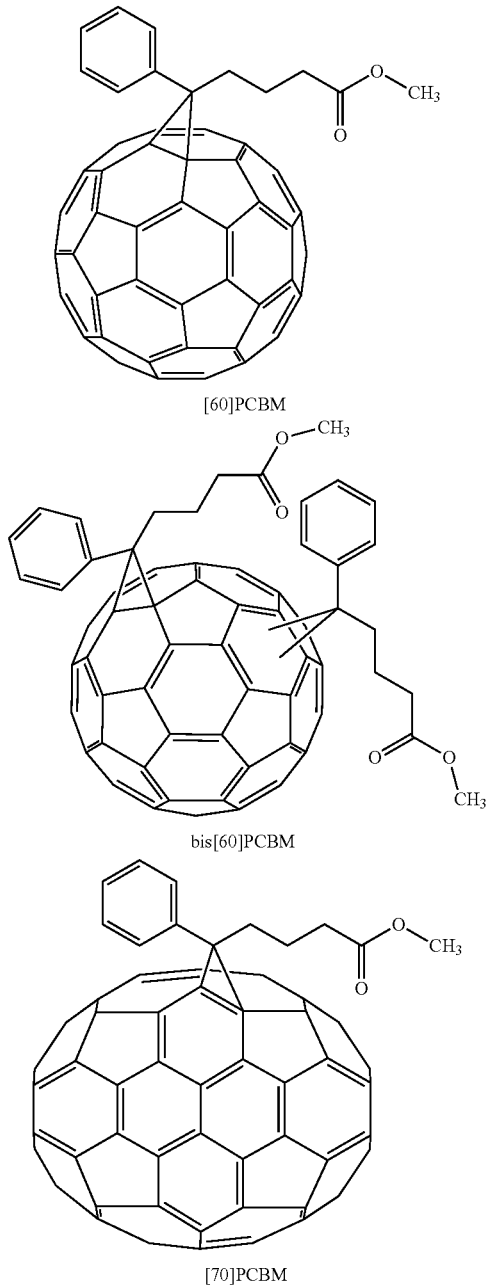

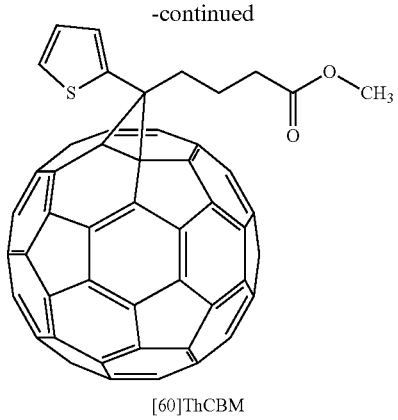
[60]ThCBM
Examples of the p-type organic semiconductor include the following organic compounds. Incidentally, the following compounds may have a substituent such as an alkyl group, in such a range as not to impair the function.
CG1
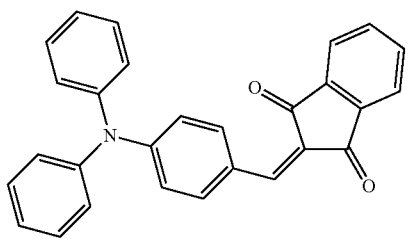
CG2
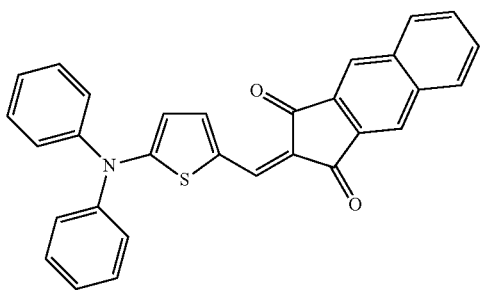
CG3
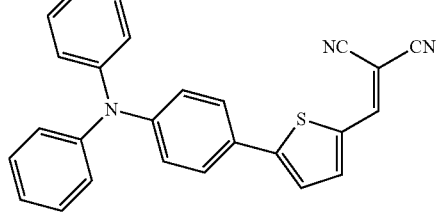
CG4
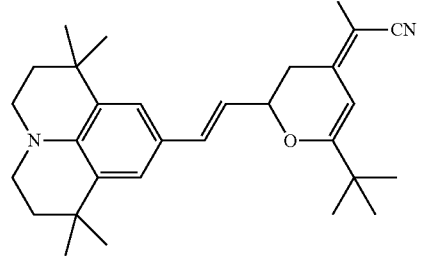
CG5
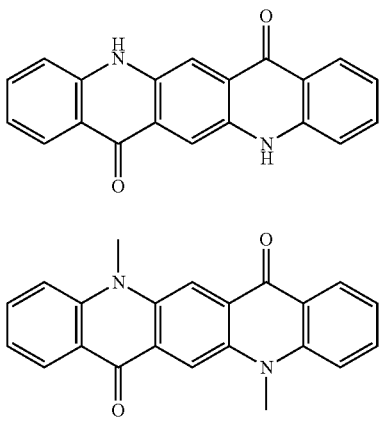
CG6
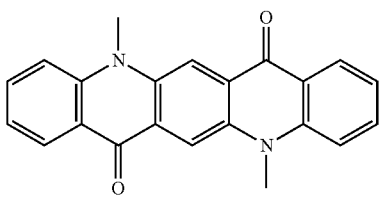
CG7
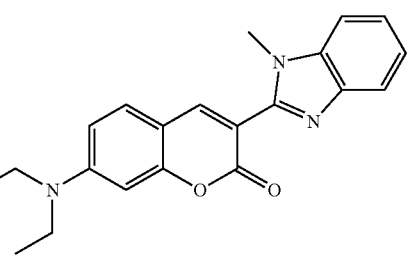
CG8
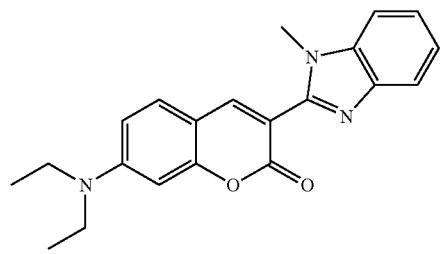
CG9
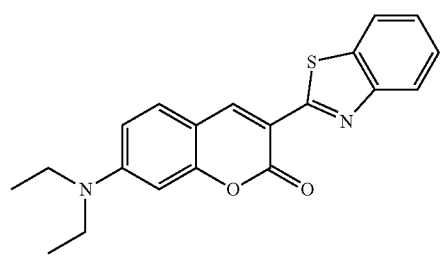
CG10
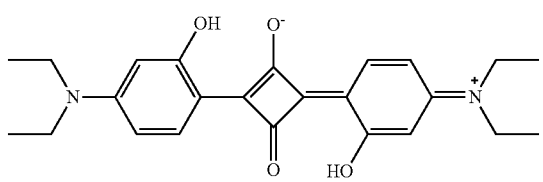
CG11
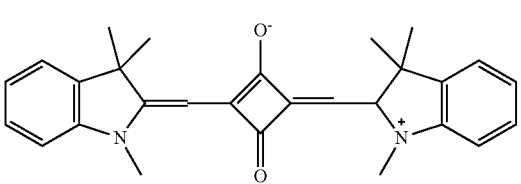

CG12
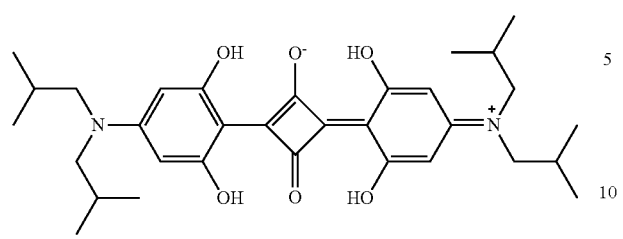
CG13
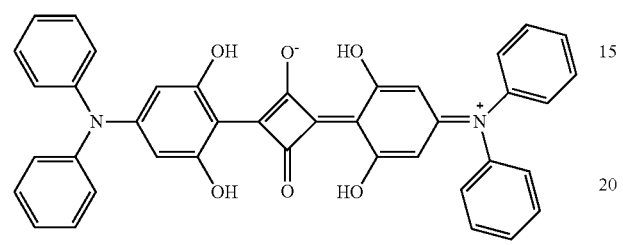
CG14
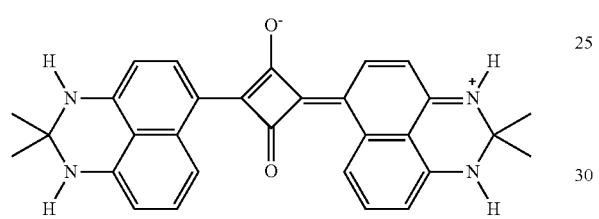
CG15
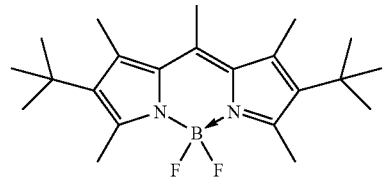
CG16
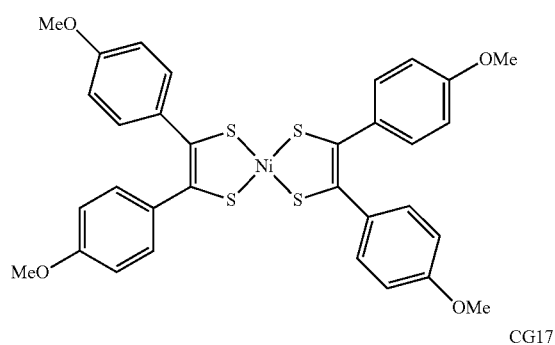
CG17
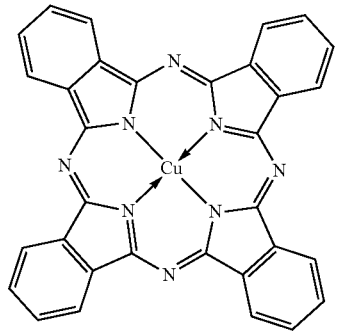
CG18
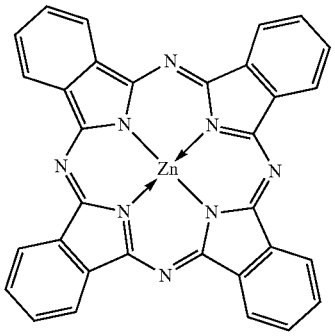
CG19
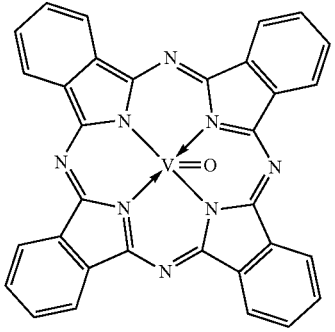
CG20
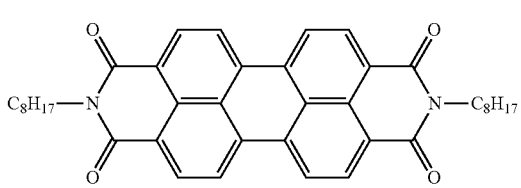
CG21
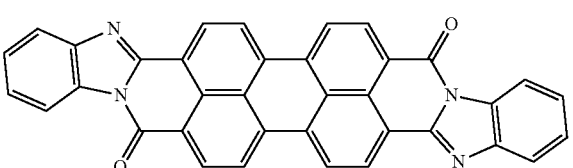
CG22
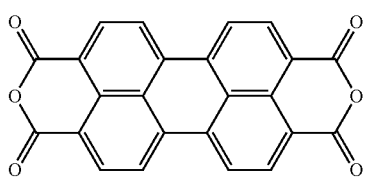
CG23
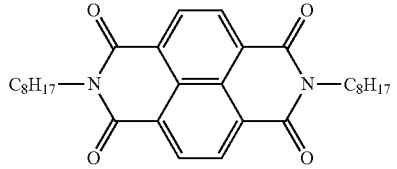
CG24
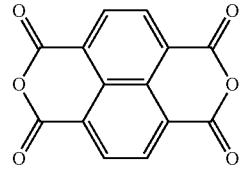

-continued

CG25
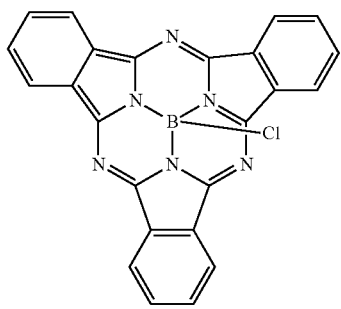

CG26
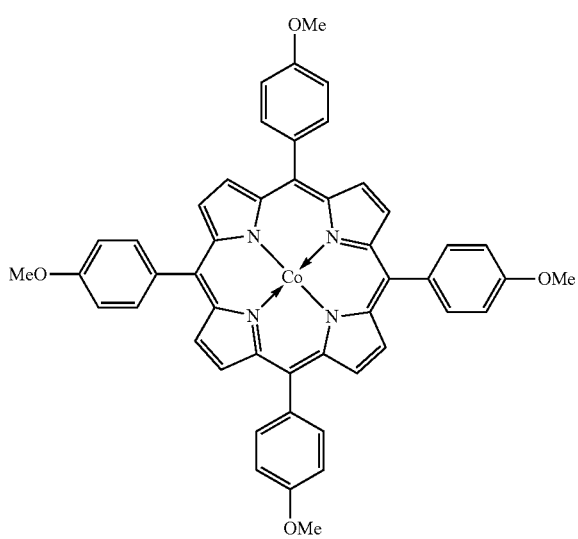

CG27
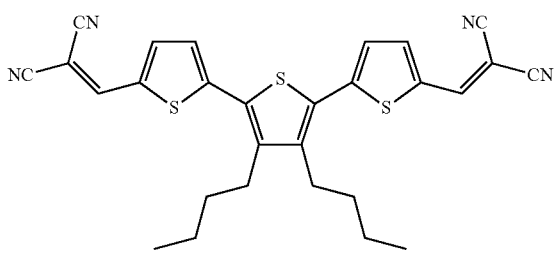

CG28
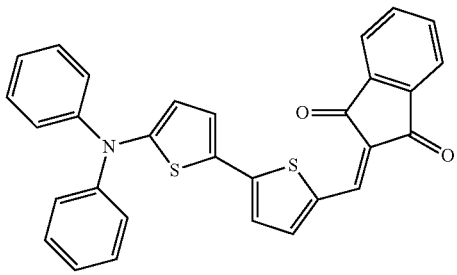

-continued

CG29
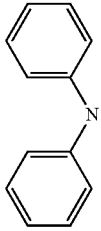

CG30
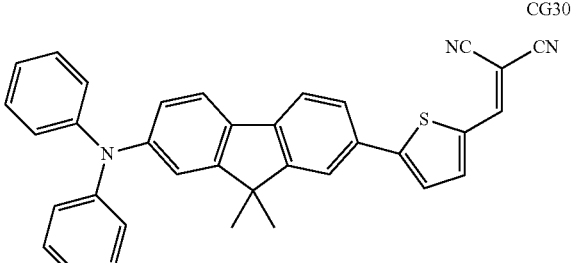

CG31
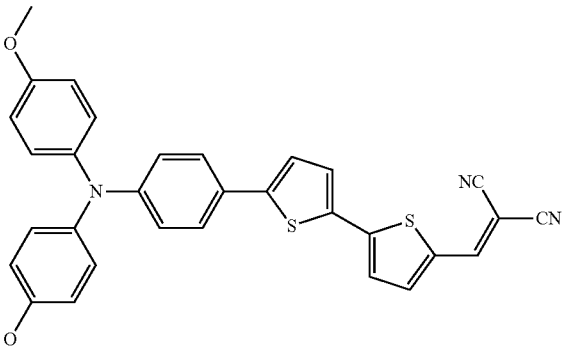

(5) Second Organic Layer (Electron Blocking Layer) 2

The second organic layer 2 is a layer for suppressing an inflow of electrons into the first organic layer 1 from the cathode 4, and has preferably a small electron affinity (close to a vacuum level). A physical property that the electron affinity is small can also mean that the LUMO is shallow. The second organic layer 2 can be referred to as an electron blocking layer because of its function. It is preferable that the second organic layer 2 is a layer which contains the organic compound of the present embodiment. The second organic layer 2 may be a plurality of layers, or may uses a bulk hetero layer (mixed layer). The cathode 4 and the second organic layer 2 may come into contact with each other, or may have another functional layer between both the cathode and the layer.

(6) Third Organic Layer (Hole Blocking Layer) 3

The third organic layer 3 is a layer for suppressing an inflow of holes into the first organic layer 1 from the anode 5, and has preferably a large ionization potential (far from the vacuum level). A physical property that the ionization potential is large can also mean that the HOMO is high. The third organic layer 3 can be referred to as the hole blocking layer, because of its function. The third organic layer 3 may be a plurality of layers, or may use a bulk hetero layer (mixed layer). The anode 5 and the third organic layer 3 may have another functional layer therebetween.

Next, the constituent material of the third organic layer 3 will be described. It is preferable that the third organic layer 3 has a high ionization potential in order to prevent holes from being injected into the first organic layer 1 from the anode 5. In addition, in order to promptly transport electrons generated in the first organic layer 1 to the anode 5, the third organic layer is preferably formed from a material having high electron mobility. In addition, in order to suppress the lowering of the film quality such as crystallization, the third organic layer is preferably formed from a material having a high glass transition temperature. The third organic layer may be a mixed layer with a material having the high glass transition temperature, from the viewpoint of improving the film quality. Specifically, the third organic layer 3 may be a mixed layer with the organic compound of the present embodiment. Specific examples of the compounds used as the hole blocking material are shown below, but, of course, the compounds are not limited thereto.

HB1

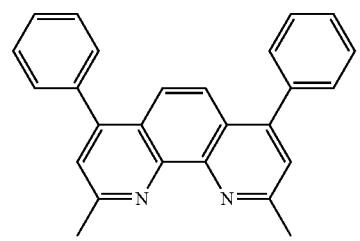

HB2

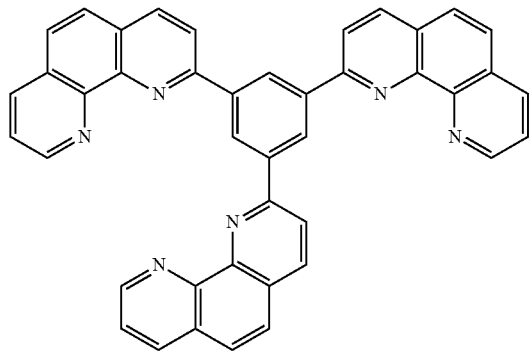

HB3

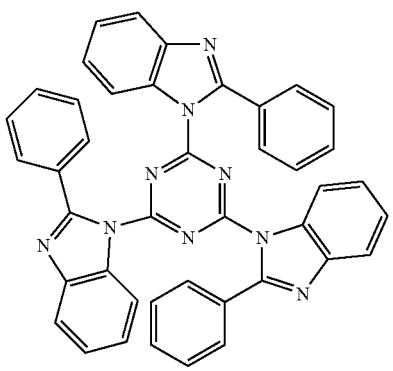

-continued

HB4

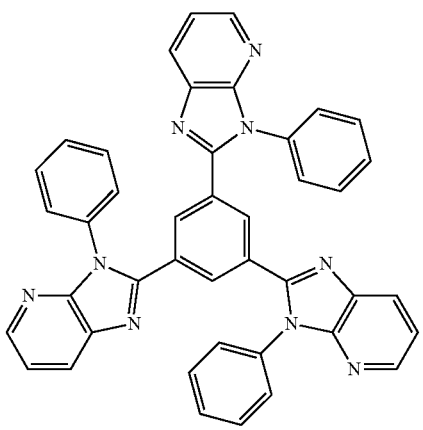

HB5

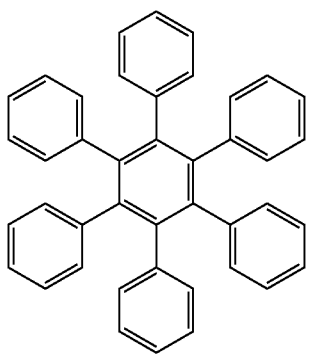

HB6

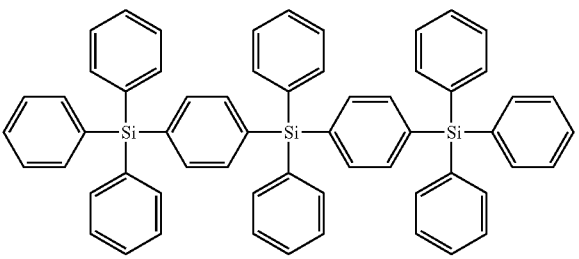

In addition to the above described compounds, fullerenes known as the n-type organic semiconductor can also be suitably used. As described above, the fullerenes are materials having an excellent electron transporting property, and accordingly can be used as the constituent material of the hole blocking layer.

(7) Protective Layer 7

The protective layer 7 is a layer formed on the upper portion of the electrode, and is preferably an insulating layer. The protective layer 7 may be formed from a single material or from a plurality of materials. When being formed from the plurality of materials, the protective layer may be formed of a plurality of stacked layers, or may be a layer in which a plurality of materials are mixed. Examples of the constituent material of the protective layer 7 include organic materials such as a resin, and inorganic materials such as silicon nitride, silicon oxide and aluminum oxide. The protective layer can be formed by a sputtering method, an ALD method (atomic layer deposition method) or the like. The silicon nitride is also described as $SiN_x$, and silicon oxide is also described as $SiO_x$. Suffix X is a numerical value representing the ratio between the elements.

A planarizing layer may be provided on the protective layer 7. The planarizing layer is provided so that the surface of the protective layer 7 does not give influence on a wavelength selecting section 8, depending on the state. The planarizing layer can be formed by a known production method, coating method, vacuum deposition method or the like. The planarizing layer may be produced by a process of CMP or the like, as needed. Examples of the material for the planarizing layer include: organic materials such as a resin; and inorganic materials such as $SiN_x$, $SiO_x$ and $Al_2O_3$. The planarizing layer may be formed from an organic compound or a mixture thereof. The forming method can include the same method as for the protective layer 7.

(8) Wavelength Selecting Section 8

The wavelength selecting section 8 is provided on the planarizing layer. When the photoelectric conversion element does not have the planarizing layer, the wavelength selecting section 8 is provided on the protective layer 7. The wavelength selecting section 8 can also be arranged on the light incident side of the photoelectric conversion element. Examples of the wavelength selecting section 8 include a color filter, a scintillator and a prism. The color filter is a filter which transmits light having a predetermined wavelength more than light having other wavelengths. For example, the color filter can cope with the whole region of visible light with the use of three types of RGB. When the three types of RGB are used, Bayer arrangement, delta arrangement or the like may be used as the arrangement of color filters. In addition, the wavelength selecting section may be a prism which separates only light having a predetermined wavelength. Incidentally, a position in which the wavelength selecting section 8 is arranged is not limited to the position shown in FIG. 1. The wavelength selecting section 8 may be arranged in any one of the optical path between the subject or the light source and the photoelectric conversion layer 1.

(9) Lens 9

A lens 9 such as a microlens is an optical member for condensing light from the outside to the first organic layer 1. In FIG. 1, a hemispherical lens is illustrated, but the shape is not limited to the shape. The lens 9 is formed of, for example, quartz, silicon, an organic resin. The shape and the material are not limited as long as the shape and the material do not obstruct the light condensing.

(10) Other Structure

The photoelectric conversion element of the present embodiment may have another photoelectric conversion element on the electrode. Another photoelectric conversion element is set as a photoelectric conversion element which photoelectrically converts light having a different wavelength, and thereby the photoelectric conversion element of the present embodiment can detect light having different wavelengths on the same or approximately the same in-plane position on the substrate.

Alternatively, the photoelectric conversion element of the present embodiment may further have another (i.e. second) organic compound layer which performs photoelectric conversion with light having a wavelength different from with which the first organic layer 1 performs photoelectric conversion; and the second organic compound layer and the first organic layer 1 may be stacked on the other. By having this structure, the photoelectric conversion element can detect light having different wavelengths, at the same position or approximately the same position on the substrate, similarly to the structure in which photoelectric conversion elements are stacked.

Imaging Device According to the Embodiment of the Present Invention and Imaging Apparatus Having the Same (1) Imaging Device The photoelectric conversion element of the present embodiment can be used for an imaging device. The imaging device includes: a plurality of photoelectric conversion elements that are light-receiving pixels; a readout circuit that is connected to each of the photoelectric conversion elements; and a signal processing circuit (signal processing section) that is connected to the readout circuit. Read-out information based on the electric charges is transmitted to the signal processing section that is connected to the imaging device. Examples of the signal processing section include a CMOS sensor or a CCD sensor. Information which each of the light-receiving pixels has acquired is collected in the signal processing section, and thereby an image can be obtained.

The imaging device includes a plurality of photoelectric conversion elements, and the plurality of photoelectric conversion elements may have different types of color filters, respectively. The plurality of types of color filters are color filters each of which transmits light having a wavelength different from others. Specifically, the color filters may have RGB color filters, respectively. The plurality of photoelectric conversion elements may have a photoelectric conversion layer as a common layer. The common layer means that a photoelectric conversion layer which one photoelectric conversion element has is connected to a photoelectric conversion layer of another photoelectric conversion element adjacent to the photoelectric conversion element.

Figure 2:
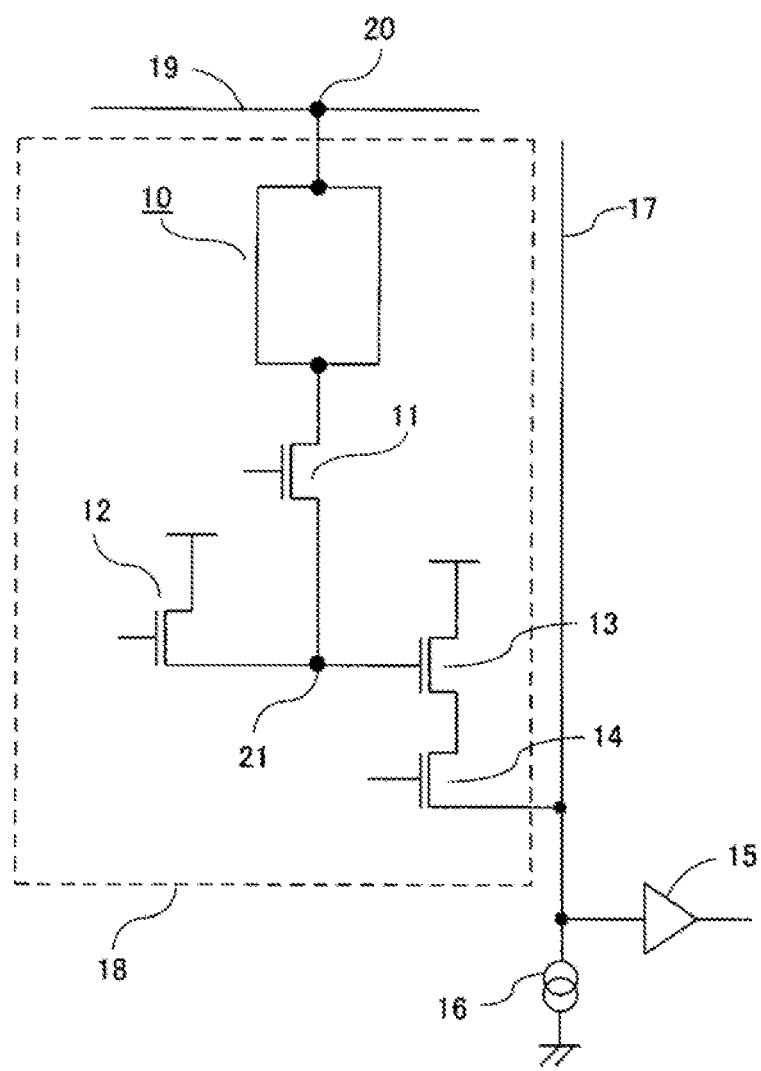
FIG. 2 is a circuit diagram of a pixel including a photoelectric conversion element according to an embodiment of the present invention.

FIG. 2 is a circuit diagram of a pixel including the photoelectric conversion element of the present embodiment. The photoelectric conversion element 10 is connected to a common wire 19 at a node A20. The common wire 19 may be connected to the ground. A pixel 18 may include the photoelectric conversion element 10, and a readout circuit for reading a signal which is generated in the photoelectric conversion section. The readout circuit may include, for example, a transfer transistor 11, an amplifying transistor 13, a selection transistor 14 and a reset transistor 12. The transfer transistor 11 is electrically connected to the photoelectric conversion element 10. The amplifying transistor 13 has a gate electrode which is electrically connected to the photoelectric conversion element 10. The selection transistor 14 selects a pixel from which the information is read out. The reset transistor 12 supplies a reset voltage to the photoelectric conversion element.

Transfer of the transfer transistor 11 may be controlled by the gate voltage. The supply of the reset potential may be controlled by the voltage which is applied to the gate of the reset transistor 12. The selection transistor 14 becomes a selective state or a nonselective state, according to the gate voltage. The transfer transistor 11, the reset transistor 12 and the amplifying transistor 13 are connected by a node B21. The pixel does not need to have the transfer transistor 11 depending on the structure. The reset transistor 12 is a transistor which supplies a voltage for resetting the potential of the node B21. The supply of the voltage can be controlled by applying a signal to the gate of the reset transistor 12. The pixel does not need to have the reset transistor 12 depending on the structure. The amplifying transistor 13 is a transistor which passes an electric current in response to the potential of the node B21. The amplifying transistor 13 is connected to the selection transistor 14 that selects the pixel 18 which outputs a signal. The selection transistor 14 is connected to a current source 16 and a column output section 15, and the column output section 15 is connected to the signal processing section. The selection transistor 14 is connected to a vertical output-signal line 17. The vertical output-signal line 17 is connected to the current source 16 and the column output section 15.

Figure 3:
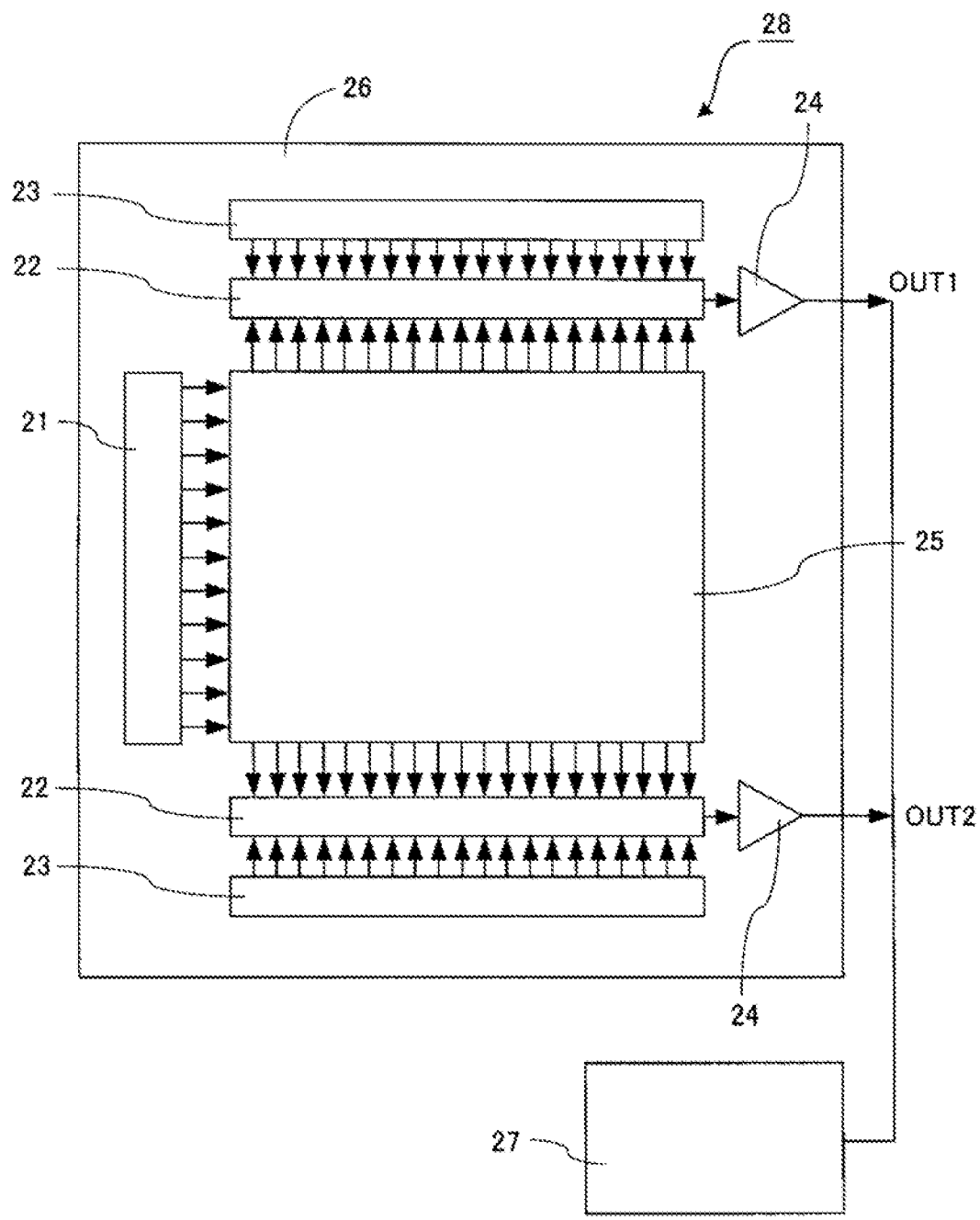
FIG. 3 is a schematic diagram illustrating an imaging device according to an embodiment of the present invention.

FIG. 3 illustrates a schematic diagram illustrating an imaging device (hereinafter referred to as "imaging device of the present embodiment") according to one embodiment of the present invention. The imaging device 28 of the present embodiment includes an imaging region 25 in which a plurality of pixels are two-dimensionally arranged, and a peripheral region 26. The region other than the imaging region 25 is the peripheral region 26. The peripheral region 26 has a vertical scanning circuit 21, a readout circuit 22, a horizontal scanning circuit 23 and an output amplifier 24; and the output amplifier 24 is connected to the signal processing section 27. The signal processing section 27 is a signal processing section which performs signal processing based on the information which is read out by the readout circuit 22; and includes a CCD circuit or a CMOS circuit.

The readout circuit 22 includes, for example, a column amplifier, a CDS circuit and an addition circuit, and performs amplification, addition and the like with respect to signals read out from the pixels in the row which is selected by the vertical scanning circuit 21, through a vertical signal line. The column amplifier, a correlated double sampling (CDS) circuit, the addition circuit and the like are arranged, for example, in each of pixel columns or of pluralities of pixel columns. The CDS circuit is a circuit for performing CDS signal processing, and performs kTC noise reduction. The horizontal scanning circuit 23 generates signals for sequentially reading the signals of the readout circuit 22. The output amplifier 24 amplifies the signal of the column which is selected by the horizontal scanning circuit 23, and outputs the resultant signal.

The above described structure is merely one structure example of the imaging device, and the imaging device of the present embodiment is not limited to the structure. The readout circuit 22, the horizontal scanning circuit 23 and the output amplifier 24 are each arranged on each of upper and lower parts which sandwich the imaging region 25 therebetween, so as to constitute two output paths. However, as for the output paths, three or more may be provided. Signals output from the output amplifiers 24 are synthesized as the respective image signals by the signal processing section 27.

(2) Imaging Apparatus

The imaging device of the present embodiment can be used for an imaging apparatus. An imaging apparatus according to one embodiment of the present invention (hereinafter referred to as "imaging apparatus of the present embodiment") includes: an imaging optical system having a plurality of lenses; and the imaging device of the present embodiment, which receives light having passed through the imaging optical system. In addition, the imaging apparatus of the present embodiment includes the imaging device of the present embodiment, and a housing that contains the imaging device therein; and the housing may have a joining portion at which the imaging optical system can join. The imaging apparatus of the present embodiment is more specifically a digital camera or a digital still camera.

In addition, the imaging apparatus of the present embodiment may have a communication section that enables a person to view the photographed image from the outside. The communication section may include a receiving section which receives a signal from the outside, and a transmitting section which transmits information to the outside. The signal which the receiving section receives is a signal for controlling at least any one of the imaging range, the start of imaging and the end of imaging, of the imaging apparatus. The transmitting section may also transmit information such as warning about an image, a remaining amount of data capacity, a remaining amount of a power supply, in addition to the photographed image. By having a receiving section and a transmitting section, the imaging apparatus can be used as a network camera.

EXAMPLE

Example 1 (Synthesis of Exemplary Compound A1)

Exemplary Compound A1 was synthesized according to a synthesis scheme which was shown below.

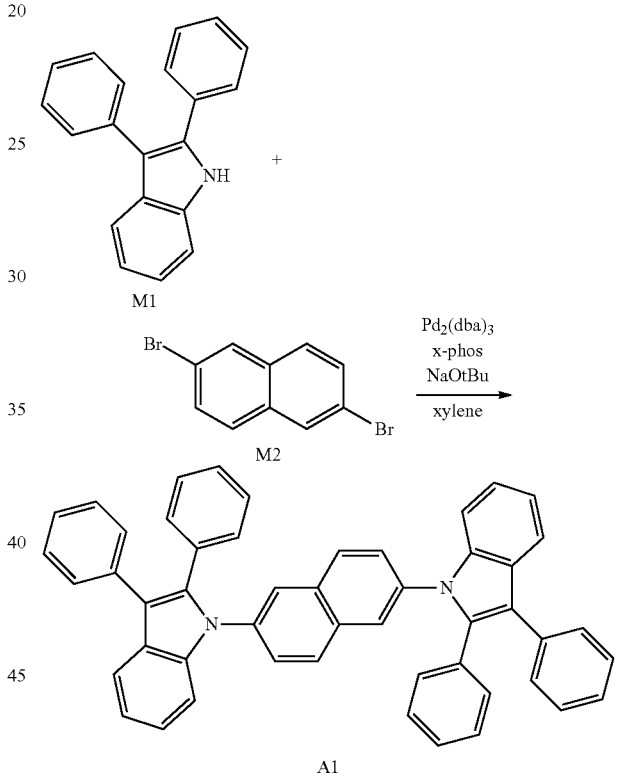

Into 100 mL of a three-necked flask which was controlled to a nitrogen atmosphere, the following reagents and solvents were sequentially charged, and the solution was stirred at room temperature for 30 minutes.

Pd$_2$(dba)$_3$: 0.16 g (0.17 mmol)
x-phos: 0.25 g (0.52 mmol)
Xylene: 35 mL

Next, the reagents and solvents which were shown below were sequentially charged.

M1: 2.07 g (7.69 mmol)
M2: 1.00 g (3.50 mmol)
Sodium tertiary butoxide: 1.11 g (11.54 mmol)

The reaction solution was heated to 130° C., and was stirred for 7 hours in a state of having been kept at 130° C. Next, the reaction solution was allowed to cool down to room temperature, and then a residue obtained by filtration was washed with water and methanol. After that, the resultant was concentrated under reduced pressure, and thereby a crude product was obtained. Next, the obtained crude product was purified by silica gel column chromatography (developing solvent: chlorobenzene solvent), was concentrated under reduced pressure, and then was washed with ethanol. The resultant product was recrystallized from a mixed solvent of toluene and heptane, and 1.55 g (yield of 67%) of Exemplary Compound A1 was obtained. The obtained Exemplary Compound A1 was identified by the following method.

<MALDI-TOF-MS (Matrix Assisted Laser Desorption Ionization-Time of Flight-Mass Spectrometry) (Autoflex LRF made by Bruker Japan K.K.)>

Actual measured value: m/z=663, and calculated value: $C_{50}H_{34}N_2$=663

<Measurement of Thermophysical Property>

A glass transition temperature of the obtained Exemplary Compound A1 was measured by DSC measurement, and the glass transition temperature was 148° C.

Example 2 (Synthesis of Exemplary Compound A4)

Exemplary Compound A4 was obtained by a synthesis which was performed by a similar method to that in Example 1, except that the following compound M3 was used in place of the compound M1.

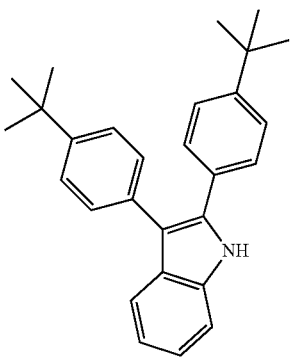

M3

The obtained compound was identified. The results are shown below.

<MALDI-TOF-MS>

Actual measured value: m/z=887, and calculated value: $C_{66}H_{66}N_2$=887

Example 3 (Synthesis of Exemplary Compound A10)

Exemplary Compound A10 was obtained by a synthesis which was performed by a similar method to that in Example 1, except that a compound M3 was used in place of the compound M1, and the following compound M4 was used in place of the compound M2.

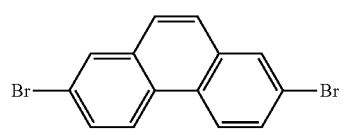

M4

The obtained compound was identified. The results are shown below.

<MALDI-TOF-MS>

Actual measured value: m/z=937, and calculated value: $C_{70}H_{68}N_2$=937

Example 4 (Synthesis of Exemplary Compound A15)

Exemplary Compound A15 was obtained by a synthesis which was performed by a similar method to that in Example 1, except that the compound M3 was used in place of the compound M1, and the following compound M5 was used in place of the compound M2.

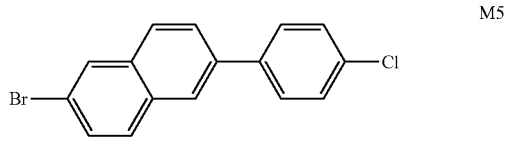 [SMILES: Clc1ccc(-c2ccc3cc(Br)ccc3c2)cc1]

M5

The obtained compound was identified. The results are shown below.

<MALDI-TOF-MS>

Actual measured value: m/z=963, and calculated value: $C_{72}H_{70}N_2$=963

Example 5 (Synthesis of Exemplary Compound B4)

Exemplary Compound B4 was obtained by a synthesis which was performed by a similar method to that in Example 1, except that the compound M3 was used in place of the compound M1, and the following compound M6 was used in place of the compound M2.

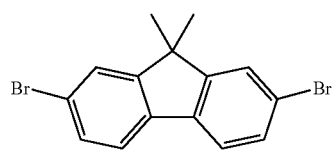

M6

The obtained compound was identified. The results are shown below.

<MALDI-TOF-MS>

Actual measured value: m/z=953, and calculated value: $C_{71}H_{72}N_2$=953

Example 6 (Synthesis of Exemplary Compound B6)

Exemplary Compound B6 was obtained by a synthesis which was performed by a similar method to that in Example 1, except that the following compound M7 was used in place of the compound M1, and the compound M6 was used in place of the compound M2.

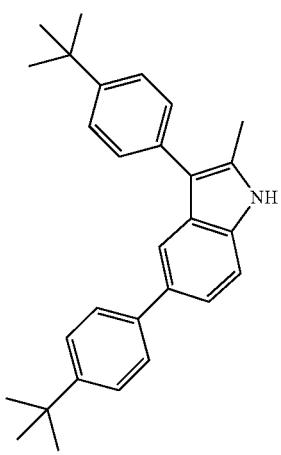

M7

The obtained compound was identified. The results are shown below.

<MALDI-TOF-MS>

Actual measured value: m/z=981, and calculated value: $C_{73}H_{76}N_2$=981

Example 7 (Synthesis of Exemplary Compound B8)

Exemplary Compound B8 was obtained by a synthesis which was performed by a similar method to that in Example 1, except that the compound M3 was used in place of the compound M1, and the following compound M8 was used in place of the compound M2.

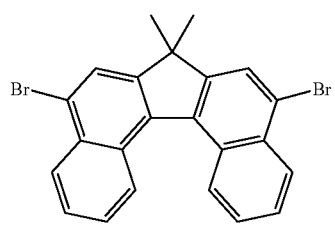

M8

The obtained compound was identified. The results are shown below.

<MALDI-TOF-MS>

Actual measured value: m/z=1053, and calculated value: $C_{79}H_{76}N_2$=1053

Example 8 (Synthesis of Exemplary Compound B10)

Exemplary Compound B10 was obtained by a synthesis which was performed by a similar method to that in Example 1, except that the following compound M9 was used in place of the compound M2.

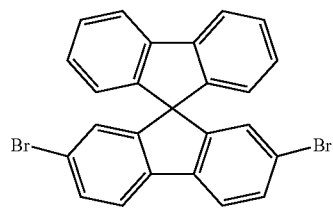

M9

The obtained compound was identified. The results are shown below.

<MALDI-TOF-MS>

Actual measured value: m/z=851, and calculated value: $C_{65}H_{42}N_2$=851

Example 9 (Synthesis of Exemplary Compound B13)

Exemplary Compound B13 was obtained by a synthesis which was performed by a similar method to that in Example 1, except that the compound M3 was used in place of the compound M1, and the compound M9 was used in place of the compound M2. The obtained compound was identified. The results are shown below.

<MALDI-TOF-MS>

Actual measured value: m/z=1075, and calculated value: $C_{81}H_{74}N_2$2=1075

Example 10 (Synthesis of Exemplary Compound B17)

Exemplary Compound B17 was obtained by a synthesis which was performed by a similar method to that in Example 1, except that the compound M3 was used in place of the compound M1, and the following compound M10 was used in place of the compound M2.

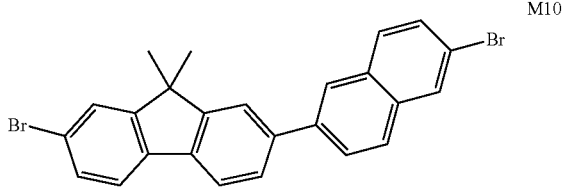 [SMILES: CC1(C)c2cc(Br)ccc2-c2ccc(-c3ccc4cc(Br)ccc4c3)cc21]

M10

The obtained compound was identified. The results are shown below.

<MALDI-TOF-MS>

Actual measured value: m/z=1080, and calculated value: $C_{81}H_{78}N_2$=1080

Example 11 (Synthesis of Exemplary Compound C3)

Exemplary Compound C3 was obtained by a synthesis which was performed by a similar method to that in Example 1, except that the compound M3 was used in place of the compound M1, and the following compound M11 was used in place of the compound M2.

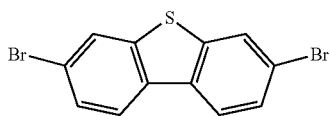

M11

The obtained compound was identified. The results are shown below.

<MALDI-TOF-MS>

Actual measured value: m/z=943, and calculated value: $C_{68}H_{66}N_2S=943$

Example 12 (Production of Photoelectric Conversion Element)

The photoelectric conversion element was produced by a method described below, in which a hole collecting electrode (cathode) 4, an electron blocking layer (second organic layer) 2, a photoelectric conversion layer (first organic layer) 1, a hole blocking layer (third organic layer) 3, and an electron collecting electrode (anode) 5 were formed in this order on a substrate.

Firstly, an indium zinc oxide was film-formed on an Si substrate, and then was patterned so as to form a desired shape; and thereby the hole collecting electrode 4 was formed. At this time, the film thickness of the hole collecting electrode 4 was set at 100 nm. The substrate on which the hole collecting electrode 4 was thus formed was used in the next step, as a substrate provided with an electrode.

Next, organic compound layers (electron blocking layer 4 photoelectric conversion layer 1 and hole blocking layer 3) and an electrode layer (electron collecting electrode 5) shown in Table 2 were continuously formed on this substrate provided with the electrode. The photoelectric conversion layer 1 was produced by co-deposition, and the mixing ratio is as shown in Table 2. At this time, an electrode area of the facing electrode (electron collecting electrode 5) was set at 3 mm².

TABLE 2

| | Constituent material | Film thickness/nm |
|---|---|---|
| Electron blocking layer | Exemplary Compound A1 | 100 |
| Photoelectric conversion layer | CG6:CG25 = 50:50 (mass ratio) | 400 |
| Hole blocking layer | Fullerene C60 | 50 |
| Electron collecting electrode | Indium zinc oxide | 30 |

Examples 13 to 23, Comparative Examples 1 and 2 (Production of Photoelectric Conversion Elements)

Photoelectric conversion elements were produced by a similar method to that in Example 12, except that the electron blocking layer, the photoelectric conversion layer and the hole blocking layer were changed as shown in Table 3. The comparative compound a-1 is the compound a-1 described in Patent Literature 3. The comparative compound b-1 is the compound b-1 described in Patent Literature 4.

TABLE 3

| | Electron blocking layer | Photoelectric conversion layer | Hole blocking layer |
|---|---|---|---|
| Example 13 | Exemplary Compound A4 | CG6:CG25 = 50:50 (mass ratio) | Fullerene 60 |
| Example 14 | Exemplary Compound A4 | CG1:Fullerene 60 = 20:80 (mass ratio) | Exemplary Compound A4:Fullerene 60 = 30:70 (mass ratio) |
| Example 15 | Exemplary Compound A10 | CG1:CG25: Exemplary Compound A10 = 40:40:20 (mass ratio) | HB2 |
| Example 16 | Exemplary Compound A15 | CG18:CG21 = 50:50 (mass ratio) | HB4 |
| Example 17 | Exemplary Compound B4 | CG1:Fullerene 60 = 30:70 (mass ratio) | Exemplary Compound B4:Fullerene 60 = 30:70 (mass ratio) |
| Example 18 | Exemplary Compound B6 | CG1:Fullerene 60 = 20:80 (mass ratio) | [60]PCBM |
| Example 19 | Exemplary Compound B8 | CG12:Fullerene 60 = 30:70 (mass ratio) | Fullerene 60 |
| Example 20 | Exemplary Compound B10 | CG1:Fullerene 60 = 20:80 (mass ratio) | Exemplary Compound B4:Fullerene 60 = 30:70 (mass ratio) |
| Example 21 | Exemplary Compound B13 | CG10:CG27 = 50:50 (mass ratio) | Exemplary Compound B4:Fullerene 60 = 30:70 (mass ratio) |
| Example 22 | Exemplary Compound B17 | CG1:Fullerene 60 = 30:70 (mass ratio) | Exemplary Compound A4:Fullerene 60 = 30:70 (mass ratio) |
| Example 23 | Exemplary Compound C3 | CG2:Fullerene 60 = 20:80 (mass ratio) | Exemplary Compound C3:Fullerene 60 = 30:70 (mass ratio) |

TABLE 3-continued

| | Electron blocking layer | Photoelectric conversion layer | Hole blocking layer |
|---|---|---|---|
| Comparative Example 1 | Comparative compound a-1 | CG6:CG25 = 50:50 (mass ratio) | Fullerene 60 |
| Comparative Example 2 | Comparative compound b-1 | CG1:Fullerene 60 = 30:70 (mass ratio) | Exemplary Compound B4:Fullerene 60 = 30:70 (mass ratio) |

Evaluation of Characteristics of Photoelectric Conversion Element

Concerning the elements obtained in Examples and Comparative Examples, the characteristics of the photoelectric conversion elements were measured and evaluated.

(1) Current Characteristics

An electric current was checked which flowed in the element when a voltage of 5 V was applied to the element. As a result, in any of the photoelectric conversion elements produced in the Examples, a ratio of the electric current in the bright place to the electric current in the dark place (electric current in bright place)/(electric current in dark place) was 100 times or more. It was confirmed that the element produced in each Example functioned as the photoelectric conversion element.

(2) Evaluation of Quantum Yield (External Quantum Efficiency) and Dark Current

Concerning the obtained photoelectric conversion elements, changes in the dark current and the external quantum efficiency before and after the annealing treatment were evaluated. An effect of reducing the dark current by annealing was evaluated in the following way: the dark current before annealing was assumed to be 1.0, and the dark current after annealing of less than 0.5 was determined to be "A", 0.5 or more and less than 1.0 was determined to be "B", and 1.0 or more was determined to be "C". In addition, the stability of the element characteristics after annealing were evaluated in the following way: the external quantum efficiency before annealing was assumed to be 1.0, and the external quantum efficiency after annealing of 1.0 or more was determined to be "A", 0.8 or more and less than 1.0 was determined to be "B", and less than 0.8 was determined to be "C". The annealing treatment was carried out by an operation of leaving the photoelectric conversion element at rest on a hot plate at 170° C. for 30 minutes in the air.

As for the dark current, a current density was measured at the time when the photoelectric conversion element was left at rest in a dark place, in a state in which a voltage of 5V was applied between the hole collecting electrode 4 and the electron collecting electrode 5.

The external quantum efficiency was calculated by an operation of measuring a density of a photocurrent which flowed when the element was irradiated with monochromatic light which had the maximum absorption wavelength of each of the elements and had an intensity of 50 μw/cm$^2$, in the state in which the voltage of 5V was applied between the hole collecting electrode 4 and the electron collecting electrode 5. The photocurrent density was obtained by subtracting the dark current density at the time when the light was shielded from the current density at the time when the light irradiated. The monochromatic light used for the measurement was light obtained by monochromatizing white light which was emitted from a xenon lamp (device name: XB-50101AA-A, made by Ushio Inc.), with a monochromator (device name: MC-10N, made by Ritu Oyo Kougaku Co., Ltd.). The voltage was applied to the element and the electric current in the element was measured both with the use of a source meter (device name: R6243, made by Advantest Corporation). In addition, light was incident vertically on the element from the side of the upper electrode (electron collecting electrode 5). The results are shown in Table 4.

TABLE 4

| | Dark current | External quantum efficiency |
|---|---|---|
| Example 12 | B | B |
| Example 13 | A | B |
| Example 14 | A | A |
| Example 15 | A | A |
| Example 16 | B | B |
| Example 17 | A | A |
| Example 18 | B | A |
| Example 19 | B | B |
| Example 20 | A | A |
| Example 21 | B | A |
| Example 22 | A | A |
| Example 23 | A | A |
| Comparative Example 1 | C | C |
| Comparative Example 2 | C | C |

It is found from Table 4 that the photoelectric conversion element of the present embodiment greatly lowers the dark current, further can also maintain the external quantum efficiency after annealing, and exhibits adequate element characteristics. On the other hand, in the photoelectric conversion element of the Comparative Example, the dark current increases after annealing. From the result, it is considered that the glass transition temperature of the material is low which forms the electron blocking layer, crystallization occurs during annealing, and thereby the film quality deteriorates, thereby lowering the element characteristics.

In addition, the external quantum efficiency in a blue region (450 nm) before the annealing treatment was compared between Example 17 and Comparative Example 2. The Example 17 and the Comparative Example 2 have the same element structure, except that the electron blocking layers are different from each other. The external quantum efficiency in Example 17 was assumed to be 1.0, and the external quantum efficiency of 1.0 or more was determined to be "A", 0.8 or more and less than 1.0 was determined to be "B", and less than 0.8 was determined to be "C". The result is shown in Table 5.

TABLE 5

| | External quantum efficiency at 450 nm |
|---|---|
| Example 17 | A |
| Comparative Example 2 | C |

It is found from Table 5 that the photoelectric conversion element of the present embodiment uses an organic compound which does not have the absorption in the visible light region, accordingly does not cause a loss by light absorption, and exhibits adequate element characteristics. On the other hand, in the photoelectric conversion element of the Comparative Example, it is considered that the external quantum efficiency is lowered particularly due to a loss by light absorption in the blue region.

As described above in the Examples, it is found that the dark current of the photoelectric conversion element can be reduced, and the thermal stability and the external quantum efficiency can be improved by an operation of making the electron blocking layer contain the organic compound of the present embodiment.

According to one embodiment of the present invention, an organic compound can be provided which does not have the absorption in the visible light region, and can adequately form the amorphous thin film that is excellent in the thermal stability and has the high glass transition temperature. Because of this, a photoelectric conversion element can be provided which is highly efficient and can suppress changes of characteristics in a process of being mounted as a photosensor, which includes high-temperature annealing treatment and a color filter forming step.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-206030, filed Oct. 25, 2017, which is hereby incorporated by reference herein in its entirety.

What is claimed is:

1. An organic compound represented by general formula (1):

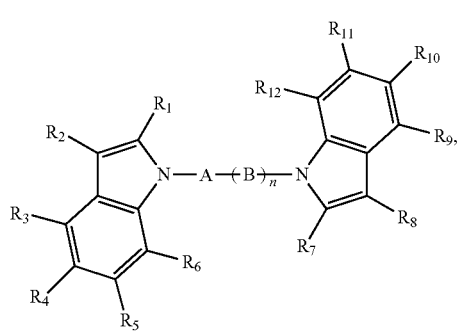

wherein:
$R_1$ to $R_{12}$ are each independently selected from the group consisting of a hydrogen atom, a halogen atom, a cyano group, an alkyl group optionally substituted with a halogen atom, an aryl group selected from the group consisting of a phenyl group, a biphenyl group, and a terphenyl group, provided that each of $R_1$, $R_2$, $R_7$, and $R_8$ is independently selected from the aryl group, which is substituted with an alkyl group having 1 to 4 carbon atoms;
wherein:
A is naphthalene, which
may have an alkyl group as a substituent;
wherein:
B is selected from the group consisting of a phenyl group and a naphthyl group; and
B may have an alkyl group as a substituent; and
wherein n is an integer of 0 to 3, and when n is 2 or larger, respective Bs may be the same as or different from each other, provided that the respective Bs are not successive phenyl groups.

2. The organic compound according to claim 1, wherein at least one of $R_1$ to $R_{12}$ is a tert-butyl group or a group having a tert-butyl group.

3. An electronic element comprising a pair of electrodes and an organic compound layer that is arranged between the pair of electrodes, wherein the organic compound layer contains the organic compound according to claim 1.

4. The organic compound according to claim 1, wherein n is 0.

5. The organic compound according to claim 1, wherein each of $R_3$, $R_5$, $R_6$, $R_9$, $R_{11}$ and $R_{12}$ is a hydrogen atom.

6. A photoelectric conversion element comprising an anode, a cathode, and an organic compound layer that is arranged between the anode and the cathode, wherein the organic compound layer contains the organic compound according to claim 1.

7. An imaging device comprising:
the photoelectric conversion element according to claim 6;
a readout circuit that is connected to the photoelectric conversion element; and
a signal processing circuit that is connected to the readout circuit.

8. An imaging apparatus comprising:
the imaging device according to claim 7; and
a housing that contains the imaging device therein,
wherein the housing has a joining portion at which an imaging optical system can join.

9. An imaging apparatus comprising:
an imaging optical system; and
an imaging device which receives light having passed through the imaging optical system,
wherein the imaging device is the imaging device according to claim 7.

10. The imaging apparatus according to claim 9, further comprising a receiving section that receives a signal from an outside, wherein the signal is a signal for controlling at least one of an imaging range, a start of imaging and an end of imaging, of the imaging apparatus.

11. The imaging apparatus according to claim 9, further comprising a transmitting section that transmits an acquired image to an outside.

12. The photoelectric conversion element according to claim 6, wherein the organic compound layer includes a photoelectric conversion layer, and the photoelectric conversion layer contains an organic n-type compound.

13. The photoelectric conversion element according to claim 12, wherein the organic compound layer includes a second photoelectric conversion layer capable of performing photoelectric conversion with light having a wavelength different from light with which the photoelectric conversion layer performs photoelectric conversion.

14. The photoelectric conversion element according to claim 12, further comprising an electron blocking layer between the cathode and the photoelectric conversion layer, wherein the organic compound layer includes the electron blocking layer, which includes the organic compound represented by the general formula (1).

15. The photoelectric conversion element according to claim 14, wherein the organic compound layer contains a hole-blocking layer disposed between the anode and the photoelectric conversion layer, and
    wherein the hole-blocking layer contains the organic compound represented by the general formula (1).

16. The photoelectric conversion element according to claim 12, wherein the organic n-type compound is fullerene, a fullerene analogue or a fullerene derivative.

17. The photoelectric conversion element according to claim 16, further comprising an electron blocking layer between the cathode and the photoelectric conversion layer, wherein the organic compound layer includes the electron blocking layer, which includes the organic compound represented by the general formula (1).

18. The photoelectric conversion element according to claim 17, wherein the organic compound layer contains a hole-blocking layer disposed between the anode and the photoelectric conversion layer, and
    wherein the hole-blocking layer contains the organic compound represented by the general formula (1).

19. An organic compound: A14:

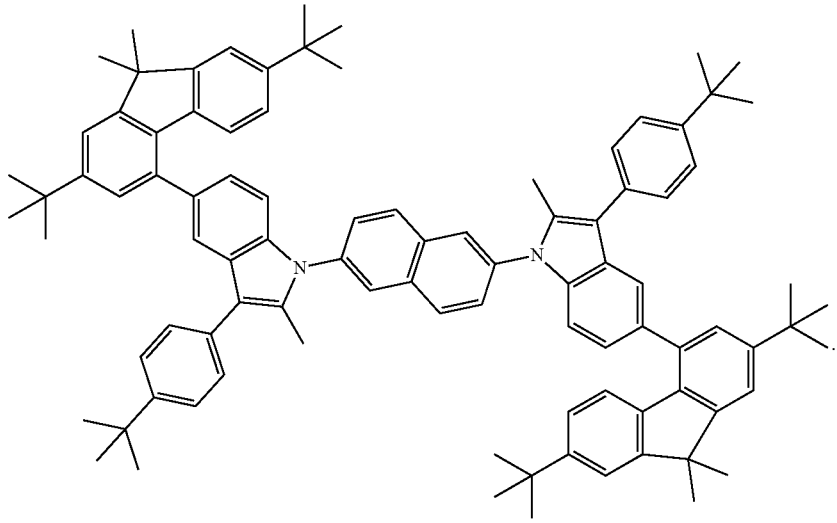

A14

20. A photoelectric conversion element comprising an anode, a photoelectric conversion layer, an electron blocking layer, and a cathode in this order, wherein the electron blocking layer contains the organic compound according to claim 19.

* * * * *